(12) United States Patent
Huber et al.

(10) Patent No.: US 9,981,034 B2
(45) Date of Patent: May 29, 2018

(54) COMPOSITIONS AND METHODS FOR VACCINATION AGAINST INFLUENZA A VIRUS

(71) Applicant: South Dakota Board of Regents, Pierre, SD (US)

(72) Inventors: Victor Huber, Vermillion, SD (US); Ying Fang, Brookings, SD (US)

(73) Assignee: South Dakota Board of Regents, Vermillion, SD (US)

( * ) Notice: Subject to any disclaimer, the term of this patent is extended or adjusted under 35 U.S.C. 154(b) by 0 days. days.

(21) Appl. No.: 15/131,989

(22) Filed: Apr. 18, 2016

(65) Prior Publication Data

US 2016/0303222 A1 Oct. 20, 2016

Related U.S. Application Data

(60) Provisional application No. 62/149,116, filed on Apr. 17, 2015.

(51) Int. Cl.
*A61K 39/145* (2006.01)
*A61K 39/12* (2006.01)
*A61K 39/00* (2006.01)

(52) U.S. Cl.
CPC ........... *A61K 39/145* (2013.01); *A61K 39/12* (2013.01); *A61K 2039/5254* (2013.01); *A61K 2039/5256* (2013.01); *A61K 2039/53* (2013.01); *A61K 2039/55* (2013.01); *A61K 2039/552* (2013.01); *A61K 2039/575* (2013.01); *C12N 2760/16121* (2013.01); *C12N 2760/16122* (2013.01); *C12N 2760/16134* (2013.01); *C12N 2760/16141* (2013.01)

(58) Field of Classification Search
None
See application file for complete search history.

(56) References Cited

U.S. PATENT DOCUMENTS

| 2008/0118531 A1* | 5/2008 | Hoffmann | A61K 39/145 424/209.1 |
| 2013/0034581 A1 | 2/2013 | Palese et al. | |
| 2013/0189303 A1 | 7/2013 | Zhou et al. | |
| 2016/0303222 A1* | 10/2016 | Huber | A61K 39/145 |

FOREIGN PATENT DOCUMENTS

| WO | WO2011044152 | 4/2011 |
| WO | WO2015042498 | 3/2015 |

OTHER PUBLICATIONS

Sequence alignment of instant SEQ ID No. 8 with Geneseq database access No. AZG98677 by Nabel et al in WO2011044152 on Apr. 2011.*

McCormick et al., "Construction and immunogenicity evaluation of recombinant influenza A viruses containing chimeric hemagglutinin genes derived from genetically divergent influenza a H1N1 subtype viruses", Jun. 10, 2015, Publisher: PLOS.

* cited by examiner

*Primary Examiner* — Shanon A. Foley
(74) *Attorney, Agent, or Firm* — Davis, Brown, Koehm, Shors & Roberts, P.C.; Sean D. Solberg; Matthew W. Coryell

(57) ABSTRACT

Disclosed herein are compositions and methods useful for immunizing a subject against disease caused by influenza A. Disclosed methods comprise administering to the subject an immunoprotective dose of an immunogenic composition. In certain aspects, the immunogenic composition is a vaccine comprised of a recombinant chimeric hemagglutinin polypeptide. In certain aspects, the subject is a mammal. In further aspects, the mammal is a pig. In still further aspects, the mammal is a human.

18 Claims, 10 Drawing Sheets

FIG. 8

A/Tennessee/1-560/2009 (H1N1)

FIG. 10

A/Iowa/01/2006 (H1N1)

COMPOSITIONS AND METHODS FOR VACCINATION AGAINST INFLUENZA A VIRUS

CROSS-REFERENCE TO RELATED APPLICATION(S)

This application claims priority from U.S. Provisional Application No. 62/149,116, filed Apr. 17, 2015, which is hereby incorporated herein by reference in its entirety for all purposes.

GOVERNMENT SUPPORT

This invention was made with government support under Grant No. 1 R15 AI090582-01 awarded by the U.S. National Institutes of Health within the Department of Health and Human Services and Project #15-020 from the National Pork Board. Accordingly, the government has certain rights in this invention.

FIELD OF THE INVENTION

Disclosed herein are compositions and methods for protecting against influenza virus infection, and in particular, vaccines comprised of chimeric hemagglutinin genes derived from genetically divergent influenza A H1N1 subtype viruses.

BACKGROUND OF THE INVENTION

Influenza A viruses infect a variety of avian and mammalian hosts, including humans and pigs, and thus pose a significant pandemic threat. Vaccines against influenza viruses are available for both pigs and humans, with human vaccines receiving annual updates based on surveillance. These vaccines are designed to limit transmission and infection with host species-restricted variants within a single influenza A virus subtype, and they demonstrate efficacy within their respective populations. However, sporadic transmissions of influenza viruses across species barriers have been noted historically, with some of these events being associated with human pandemics. Since 2009, the emergence and pandemic classification of a triple reassortant influenza A virus (H1N1 subtype) containing swine, human, and avian genetic components raised greater concerns over future pandemics of swine-origin viruses. Specifically, there is a possibility that novel viruses could evolve within swine populations to yield viruses with increased transmissibility and virulence within humans. Since vaccination remains the primary means for controlling seasonal influenza viruses, combining our efforts to limit interspecies transmission events represents a likely path toward development of a pandemic vaccine. A vaccine that could limit the circulation of influenza viruses among pigs, as well as prevent interspecies transmission events from pigs to humans, would strengthen these efforts.

Seasonal influenza vaccines have historically demonstrated moderate effectiveness when the circulating strains closely match the vaccine strain, and the success of the vaccine can be compromised when there is not a close match. Efforts to generate vaccines that match circulating strains can be time-consuming, and in pigs the reformulation process of swine influenza vaccines is limited by the high cost of surveillance. Thus, a vaccine that can induce strong, broad, protective immunity toward heterologous strains is urgently needed in both pigs and humans.

BRIEF SUMMARY OF THE INVENTION

Disclosed herein is a method of immunizing a subject against disease caused by influenza A comprising administering to the subject an immunoprotective dose of an immunogenic composition, wherein the immunogenic composition comprises a polypeptide having at least 90% sequence identity to SEQ ID NO 8. In certain aspects, the subject is a mammal. In further aspects, the mammal is a pig. In still further aspects, the mammal is a human.

Disclosed herein is an immunogenic composition comprising a polypeptide having at least 90% sequence identity to SEQ ID NOs 1-9. According to certain aspects, the immunogenic composition is a recombinant polypeptide. In certain aspects, the immunogenic composition comprises a polypeptide having at least 90% sequence identity to SEQ ID NO 8. In further aspects, the immunogenic composition further comprises a vector. In still further aspects, the vector further comprises a virus backbone. In yet further aspects, the virus backbone is $PR8_{LAIV}$ or TX98.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

FIG. 8 shows alignment of the chimeric HAs with A/Tennessee/1-560/2009 (H1N1) (SEQ ID NO 10).

FIG. 10 shows alignment of the chimeric HAs with A/Iowa/01/2006 (H1N1) (SEQ ID NO 13).

DETAILED DESCRIPTION

Figure 1:
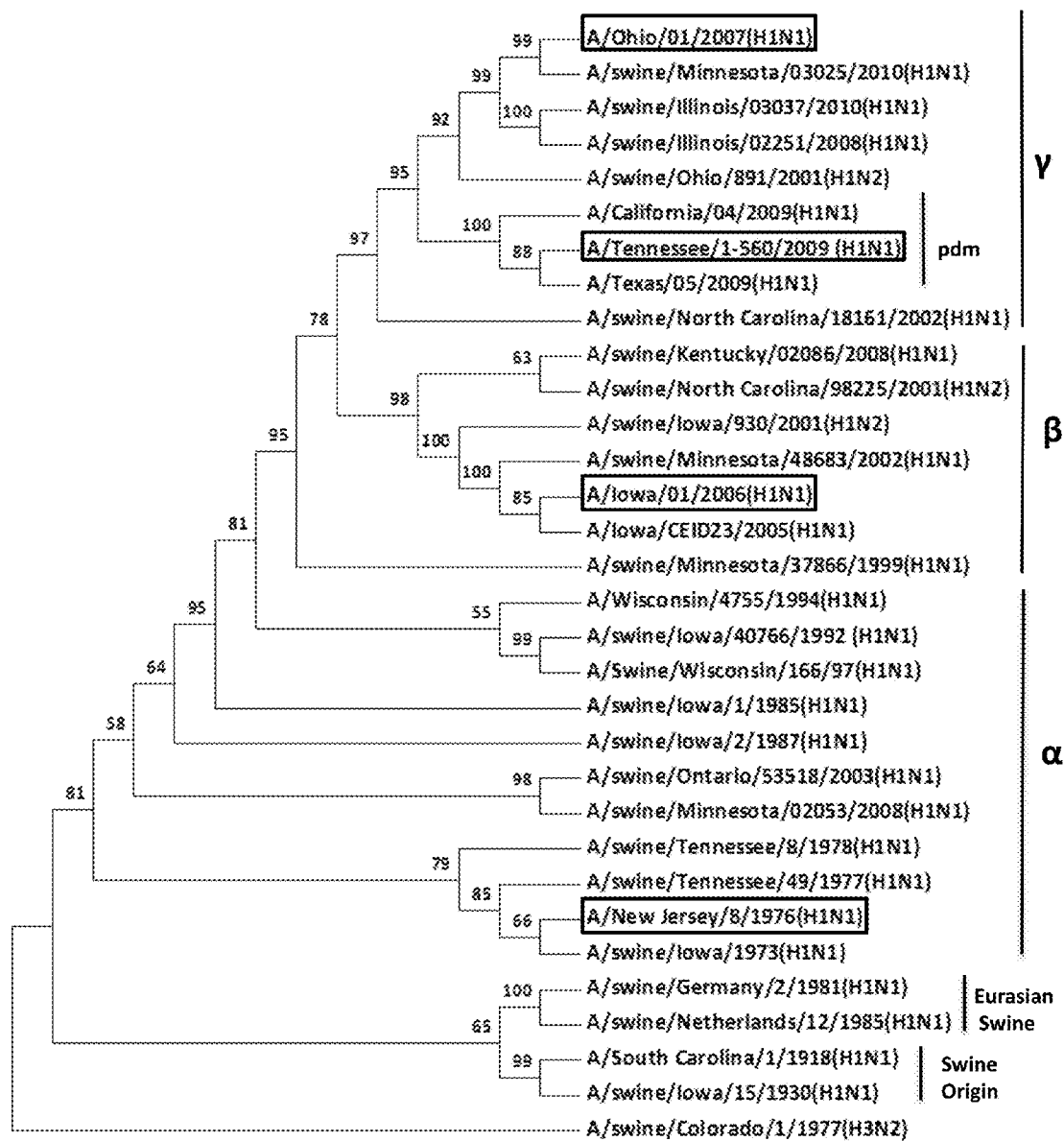
FIG. 1 shows a phylogenetic comparison of swine H1 influenza hemagglutinins, including those used to create chimeric HAs, according to certain embodiments.

A molecular breeding (DNA shuffling) strategy represents a novel approach to produce broadly protective vaccines.

DNA shuffling is a process of random recombination of parental genes into novel genes, with shuffled (recombined) chimeric genes being selected for desired properties. The importance of this process is that molecular breeding by DNA shuffling of specific genes mimics the evolution pathway and accelerates the natural process of evolution for viruses, or viral proteins, in vitro. In the instant disclosure, molecular breeding technology was applied toward producing a broadly protective vaccine against influenza A virus in pigs. Since the viral surface glycoprotein HA has been the major target of most licensed influenza vaccines, we specifically targeted the HA from the 2009 pandemic virus, as well as HAs from three additional swine influenza viruses that had a history of zoonotic transmission to humans. These parental influenza A H1N1 strains represent four distinct phylogenetic clades, and HA genes of these four parental strains were used for DNA shuffling and screening to generate a panel of chimeric influenza HA antigens. One chimeric construct, HA-129, was further presented in the context of a traditional, whole virus vaccine backbone, and immune responses induced by this chimera were evaluated in both mice and pigs. The instantly disclosed results indicate chimeric HA antigens generated by DNA shuffling have potential applications as broadly protective influenza vaccines.

A previous study reported that multiple, individual human influenza hemagglutinins (HAs), from the H3N2 subtype, could be delivered simultaneously to induce immunity that covered approximately 20 years of HA evolution. (See, Huber V C, et. al., *A Multi-Valent Vaccine Approach that Elicits Broad Immunity Within an Influenza Subtype*, 27 VACCINE 1192-1200 (2009)). This proof-of-concept approach showed that broad immunity can be achieved, within an influenza A virus subtype. However, delivery of distinct HAs by simultaneously inoculating with multiple whole virus preparations did not induce detectable antibody titers against all of the HAs included. Thus, improvement on this approach is needed.

The following definitions and methods are provided to better define the invention and to guide those of ordinary skill in the art in the practice of the present invention. Unless otherwise noted, terms are to be understood according to conventional usage by those of ordinary skill in the relevant art.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

An "immunogenic composition" as used herein, means an antigenic component which elicits an "immunological response" in the host with a cellular and/or antibody-mediated immune response to such a component. Preferably, this immunogenic composition is capable of conferring protective immunity against infection against a selected pathogen and the clinical signs associated therewith. In some forms, immunogenic portions of the native virus in a killed or inactivated form are used as the antigenic component in such compositions.

An "individual" or "subject" or "animal", as used herein, refers to vertebrates that support a negative strand RNA virus infection, specifically influenza virus infection, including, but not limited to, birds (such as water fowl and chickens) and members of the mammalian species, such as canine, feline, lupine, mustela, rodent (racine, murine, etc.), equine, bovine, ovine, caprine, porcine species, and primates, the latter including humans. In a specific embodiment, the subject is a pig. In another embodiment, the subject is a human.

As used herein, the term "immunogenic" means that the virus or polypeptide is capable of eliciting a humoral or cellular immune response, and preferably both. An immunogenic entity is also antigenic.

The terms "effective amount" or "pharmaceutically effective amount" of an immunogenic composition of the present invention refer herein to a sufficient amount of the immunogenic composition to treat or diagnose a condition of interest. The exact amount required will vary from subject to subject, depending, for example, on the species, age, and general condition of the subject; the severity of the condition being treated; the particular antigen of interest; in the case of an immunological response, the capacity of the subject's immune system to synthesize antibodies, for example, and the degree of protection desired; and the mode of administration, among other factors. An appropriate "effective" amount in any individual case may be determined by one of ordinary skill in the art. Thus, a "therapeutically effective amount" will typically fall in a relatively broad range that can be determined through routine trials.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18$^{th}$ Edition.

As used herein, the term "adjuvant" refers to a compound or mixture that enhances the immune response to an antigen. An adjuvant can serve as a tissue depot that slowly releases the antigen and also as a lymphoid system activator that non-specifically enhances the immune response (Hood, et al., *Immunology, Second Ed.*, Menlo Park, Calif.: Benjamin/Cummings, 1984. p. 384). Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, and potentially useful human adjuvants such as N-acetyl-muramyl-L-threonyl-D-isoglutamine (thr-MDP), N-acetyl-normuramyl-L-alanyl-D-isoglutamine, N-acetylmuramyl-L-alanyl-D-isoglutaminyl-L-alanine-2-(1'-2'-dipalmitoyl-sn-glycero-3-hydroxyphosphoryloxy)-ethylamine, BCG (bacille Calmette-Guerin), and *Corynebacterium parvum*. Preferably, the adjuvant is pharmaceutically acceptable.

The terms "killed" or "inactivated" are used interchangeably herein and refer to a significant or complete reduction in the infectivity of the virus(es) utilized for preparation of the vaccine compositions. The killing or inactivation of the viruses may be evaluated according to any procedure known to those skilled in the art, for example, by molecular biology methods (PCR), methods for titration of the viral titer, fluorescence, immunological methods (ELISA, RIA and the like), or immunoenzymatic methods allowing the detection of one or more viral polypeptides (Western and the like). A number of different inactivating agents and means have been employed including formalin, azide, freeze-thaw, sonication, heat treatment, sudden pressure drop, detergent (especially non-ionic detergents), lysozyme, phenol, proteolytic enzymes, and beta-propiolactone.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M Stockton Press, New York, 1991; and Carillo, H., and Lipman, D., SIAM J. APPLIED MATH., 48:1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al 1984), BLASTP, BLASTN, and FASTA (Altschul, S. F., et al., 1990). The BLASTX program is publicly available from NCBI and other sources (BLAST Manual, Altschul, S., et al., NCBI NLM NIH Bethesda, Md. 20894; Altschul, S., et al., 1990). The well-known Smith Waterman algorithm may also be used to determine identity.

By way of example, without intending to be limited thereto, an amino acid sequence of the present invention may be identical to the reference sequences SEQ ID NOS: 1-9; that is be 100% identical, or it may include a number of amino acid alterations as compared to the reference sequence such that the % identity is less than 100%. Such alterations are selected from the group consisting of at least one amino acid deletion, substitution, including conservative and non-conservative substitution, or insertion, and wherein the alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in SEQ ID NOS:1-9 by the numerical percent of the respective percent identity (divided by 100) and then subtracting that product from said total number of amino acids in any of SEQ ID NOS: 1-9, or:

$$n_a = X_a - (X_a \cdot Y),$$

wherein $n_a$ is the number of amino acid alterations, $X_a$ is the total number of amino acids in SEQ ID NOS: 1-9, and Y is, for instance 0.70 for 70%, 0.80 for 80%, 0.85 for 85% etc., and wherein any non-integer product of $X_a$ and Y is rounded down to the nearest integer prior to subtracting it from $X_a$.

In preferred embodiments, the polypeptide above is selected from the proteins set forth in the SEQ ID NOS 1-9.

Disclosed herein is an immunogenic composition comprising a polypeptide having at least 90% sequence identity to SEQ ID NOs 1-9. According to certain aspects, the immunogenic composition is a recombinant polypeptide. In certain aspects, the immunogenic composition comprises a polypeptide having at least 90% sequence identity to SEQ ID NO 8. In further aspects, the immunogenic composition further comprises a vector. In still further aspects, the vector further comprises a virus backbone. In yet further aspects, the virus backbone is PR8$_{LAIV}$ or TX98.

According to certain embodiments, the vector is a non-influenza virus. Exemplary non-influenza virus vectors include, but are not limited to, retrovirus, lentivirus, adenovirus, adeno-associated virus, parainfluenza virus, or other virus vectors known in the art to be suitable for the delivery of recombinant proteins.

According the certain aspects, the disclosed immunogenic composition further comprises an adjuvant. In yet further aspects, the immunogenic composition further comprises a pharmaceutically acceptable carrier.

Disclosed herein is a method of immunizing a subject against disease caused by influenza A comprising administering to the subject an immunoprotective dose of an immunogenic composition, wherein the immunogenic composition comprises a polypeptide having at least 90% sequence identity to SEQ ID NO 1-9. According to certain aspects, the immunogenic composition comprises a polypeptide having at least 90% sequence identity to SEQ ID NO 8.

In certain aspects, the subject is a mammal. In further aspects, the mammal is a pig. In still further aspects, the mammal is a human.

According to certain aspects, the immunogenic composition is administered at a therapeutically effective amount. In further aspects, the immunogenic composition is administered at a prophylactically effective amount.

In still further aspects, the immunogenic composition further comprises a virus backbone. In yet further aspects, the immunogenic composition is an attenuated virus. In further aspects, the immunization elicits immune response against α, β, γ, and pandemic strains of classical swine virus.

EXAMPLES

The following examples are put forth so as to provide those of ordinary skill in the art with a complete disclosure and description of certain examples of how the compounds, compositions, articles, devices, and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the invention.

Materials and Methods

Parental HA Genes and Viral Strains

The HA genes of the four parental H1N1 influenza A viruses A/Tennessee/1-560/09 (TN09; CY040457.1), A/New Jersey/8/1976 (NJ76; CY130118.1), A/Ohio/01/2007 (OH07; FJ986620.1), and A/Iowa/01/2006 (IA06; FJ986618.1) were amplified by RT-PCR from stock viruses using the Bm-HA-1F (TATTCGTCTCAGGGAG-CAAAAGCAGGGG) (SEQ ID NO 14) and Bm-NS-890R (ATATCGTCTCGTATTAGTAGAAACAAGGGTGTTTT) (SEQ ID NO 15) primers as described [26,27]. The PCR products were cloned in pHW2000 plasmid using BsmBI restriction enzyme sites [28]. Additional H1N1 influenza A virus strains that were tested to demonstrate cross reactivity include A/North Carolina/18161/2002 (NC02; CY098516.1), A/swine/Iowa/i/1985 (IA85; CY022317.1), A/swine/Iowa/40766/1992 (IA92; KP788773), A/swine/Germany/2/1981 (GE81; Z30276.1), and A/New Caledonia/20/99 (NC99; CY125100.1).

DNA Shuffling of HA Genes

The DNA shuffling of HA genes was performed as described by Soong et al [29] with minor modifications. Briefly, DNA products of HA genes from the four parental strains (TN09, NJ76, OH07, and IA06) were mixed equimolarly and digested with DNase I. The DNA fragments were assembled as described previously [23], and the reassembled fragments were amplified by PCR using the Bm-HA-1F (TATTCGTCTCAGGGAGCAAAAGCAGGGG) (SEQ ID NO 14) and Bm-NS-890R (ATATCGTCTCGTATTAGTA-GAAACAAGGGTGTTTT) (SEQ ID NO 15) primers. The PCR products were cloned into the pHW2000 plasmid to establish the chimeric HA library.

Creation and Characterization of HA-Expressing Virus Reassortants

The 8-plasmid reverse genetics system, incorporating co-cultured 293T (American Type Culture Collection, Manassas, Va.) and MDCK (ATCC) cells, was used to create reassortant viruses in this study [27]. For viruses expressing the cloned parental HA genes from TN09, OH07, NJ76, or IA06, the viruses were created using reverse genetics, with each HA incorporated into a reassortant virus that derived the 7 other influenza virus genes from the A/Puerto Rico/8/34 (PR8) donor virus [30,31]. Viruses rescued from 293T:MDCK cell co-cultures that expressed the desired HA were propagated in 10-day-old embryonated chicken eggs for 72 h at 35° C. and sequenced to verify appropriate HA genotype. Similarly, when expressing the chimeric HA construct, HA-129, within influenza viruses for vaccine creation, we used the attenuated PR8 ($PR8_{LAIV}$) backbone for generating a candidate vaccine in mouse ($PR8_{LAIV}$-129), while the A/swine/Texas/4199-2/98 swine reverse genetics system was used for generating a candidate inactivated influenza virus (IIV) vaccine in pigs (TX98-129) [32].

Viruses ($PR8_{LAIV}$-129) rescued on the $PR8_{LAIV}$ backbone were propagated in 10-day-old embryonated chicken eggs for 72 h at 33° C., as described previously [13,33], and the TX98-129 virus was propagated for 72 h at 35° C. The growth characteristics of these viruses were determined using MDCK cells as previously described [34]. Briefly, MDCK cell monolayers ($3 \times 10^5$ cells per well) were inoculated with influenza viruses in the presence of TPCK-trypsin [34], and at indicated times, amounts of virus present were tested using standard methods for calculating the median tissue culture infectious dose ($TCID_{50}$) of influenza viruses [35].

Mice and Immunization

Adult (6-8-week-old) female BALB/cJ mice were obtained from Harlan Laboratories (Indianapolis, Ind.) and housed in groups of four, with 24-hour access to food and water. All animal experiments were performed following the guidelines established and approved by the Animal Care and Use committee at the University of South Dakota (Vermillion, S. Dak.). For DNA immunization, plasmid DNA was coupled to gold particles as described previously [36], and administered directly to the mouse abdomen, using a Helios gene gun (Bio-Rad Laboratories, Hercules, Calif.). Mice were boosted twice with a 3-week interval between inoculations. Three weeks after the third inoculation, sera were collected and analyzed by ELISA. For whole virus vaccination, mice that were lightly anesthetized with 2.5% isoflurane were inoculated with $1 \times 10^5$ $TCID_{50}$ $PR8_{LAIV}$-129 in a 50 μl volume, and boosted with $1 \times 10^5$ $TCID_{50}$ $PR8_{LAIV}$-129 at 28 days post inoculation (dpi). Sera were collected at 21 days after the second inoculation with whole virus. To inactivate host innate immune inhibitors of influenza virus, sera were treated with receptor-destroying enzyme (RDE, Accurate Chemical, Westbury, N.Y.) and heat-inactivated as described previously [37].

Antibody detection by ELISA

Serum antibodies were detected using an ELISA, as described previously [13]. Briefly, 96-well flat bottom plates (NUNC, Thermo Fisher Scientific) were coated with concentrated, formalin-inactivated parental viruses (1 μg HA $mL^{-1}$). RDE-treated sera were serially diluted in phosphate buffered saline (PBS) containing 10% fetal bovine serum (FBS) (Atlanta Biologicals, Lawrenceville, Ga.) and 0.05% (v/v) Tween-20 (Sigma, St. Louis, Mo.) (FBS-PBST). Alkaline phosphatase-conjugated preparations of goat anti-mouse IgG (γ-specific) antibodies (Southern Biotechnology, Inc., Birmingham, Ala.), diluted in FBS-PBST, were added to the plate. Plates were washed, and 1 mg $mL^{-1}$ p-nitrophenyl phosphate substrate (Sigma, St. Louis, Mo.) in diethanolamine buffer was added. One hour after substrate addition, the OD was detected at 405 nm using a BioTek EL808 plate reader (BioTek Instruments, Inc.). Reciprocal serum antibody titers for individual sera are reported at 50% maximal binding on the individual titration curves. Individual sera were considered positive only if their starting dilution $OD_{405}$ values were greater than 3 times the $OD_{405}$ of negative control sera.

Hemagglutination Inhibition and Microneutralization Assays

Hemagglutination inhibition (HAI) assays were performed as described previously [37]. Briefly, RDE-treated sera were diluted serially, and four HA units of virus were added to each well. The virus:sera mixtures were incubated for one hour at 4° C., and a 0.5% solution of chicken red blood cells (Lampire Biological Laboratories, Piersville, Pa.) was added to each well. Titers are reported as the reciprocal of the final serum dilution that inhibited hemagglutination. Similarly, microneutralization (MN) assays were performed as previously described [34,37], using 100 $TCID_{50}$ for each virus inoculated onto confluent MDCK monolayers. Infected MDCK cells were identified using monoclonal antibodies against the influenza A virus nucleoprotein, with a titer defined as the last dilution that inhibited detection of NP below 50% of the $OD_{490}$ for positive control wells, as described previously [38,39]. For both HAI and MN assays, serum samples that did not show a detectable titer at the starting serum dilution of 1:10 were assigned a titer of 5 for the purpose of both graphing and statistical analyses.

Nursery Pig Study

Nursery pigs (3 weeks old) that were free of swine influenza virus, porcine reproductive and respiratory syndrome virus, and *Mycoplasma hyopneumoniae* were obtained. They were randomly divided into three groups, and housed separately in animal isolation facilities at South Dakota State University (SDSU). In contrast to the murine model, live influenza virus was not given to pigs, due to biosafety considerations. Therefore, TX98-129 virus was formalin-inactivated as described previously [40], and pigs were immunized intramuscularly with 100 µg/ml of inactivated virus in a 2 mL volume. As a negative control, a group of unvaccinated pigs were inoculated with a similar volume of PBS. Fourteen days after primary inoculation, pigs were boosted with the same dose of antigen, and sera were collected at 14 days post-secondary inoculation.

Data Analysis

DNASTAR and MEGA4 were used for sequence alignment and phylogenetic analysis. Table 1 lists all the influenza virus strains from which HA genes were used for constructing the phylogenetic tree. Analysis of HA chimeras created by DNA shuffling was performed by using the Salanto method (https://bitbucket.org/benderc/salanto/wiki/Home). Two way analysis of variance and nonparametric Mann Whitney tests were used to analyze the data. Significant differences between groups were evaluated using Bonferroni post-tests. All statistical analyses were performed using either JMP 5.1 (SAS Institute, Cary, N.C.) or GraphPad Prism version 4.00 for Windows (GraphPad Software, San Diego Calif. USA, www.graphpad.com).

Results

Construction and Screening of Chimeric HA Genes

As shown in FIG. 1, based on the phylogenetic analysis of influenza A H1 HA genes, four distinct parental influenza virus strains were selected for generating chimeric HA constructs. Specifically, the selection consisted of A/Tennessee/1-560/2009 (TN09; 2009 human pandemic vaccine strain), A/Ohio/1/2007 (OH07; zoonotic isolate), A/Iowa/1/2006 (IA06; zoonotic isolate), and A/New Jersey/8/1976 (NJ76; zoonotic isolate included in the 1976 pandemic vaccine). Each of these represents one of the major phylogenetic clades of classical swine ($\alpha$, $\beta$, and $\gamma$) and recent pandemic (pdm) strains, as defined previously [25]. Since analysis of influenza viruses diversity based solely on genetic distance does not fully recapitulate the antigenic differences observed for influenza virus HA proteins, initially, a hemagglutination inhibition (HAI) assay was performed to evaluate antibodies induced against each of the parental HA proteins expressed on a PR8 background. As shown in Table 2, reactivity of sera against homologous HA-expressing virus was at least four-fold higher than that against heterologous HA-expressing viruses. The antigenic distance between the parental HA proteins was calculated using the HAI titers and the criteria described by Cai et al [41]. As shown in Table 3, the closest antigenic distance for any of our selected parental HA proteins was at least 10-fold, which is greater than the four-fold antigenic difference that is used to define distinct isolates during vaccine selection. Notably, the IA06 parental HA expressed on a PR8 background induced a strong antibody response against both the homologous HA and heterologous parental HAs (Table 2). Despite this high immunogenicity, the antigenic distance calculated for IA06 (Table 3) still indicated distinct antibody reactivity for this parental HA. Together, these data indicate that the viruses selected are both genetically and antigenically distinct.

Figure 2:
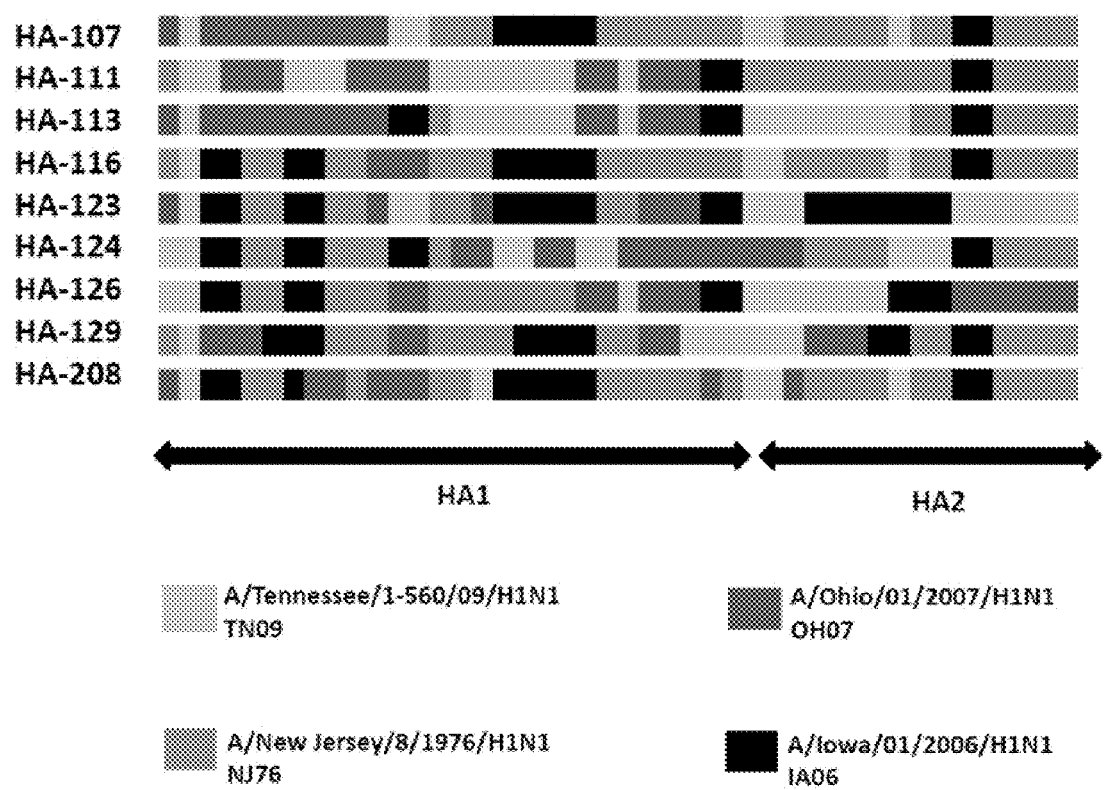
FIG. 2 shows a schematic diagram of DNA shuffled chimeric HA gene sequences, according to certain embodiments.

Subsequently, chimeric HA genes from these four parental viruses were constructed. HA genes were molecularly bred using the DNA shuffling method. A total of 33 chimeric HA genes were generated, and these shuffled HA constructs were cloned into the pHW2000 plasmid to establish an influenza HA antigen library. Using a DNA shuffling alignment analysis tool [42], these HA constructs were evaluated for representative parental gene fragments within the chimeric sequence, as shown in FIG. 2. As shown in FIGS. 7-10, individual alignments were also created to compare the HA1 region of each parental HA with the chimeric HA constructs, which shows amino acids differences in antigenic sites and the receptor-binding site (RBS). Nine constructs that contain the genetic elements from HA genes of all four parental viruses were selected for further analysis, including HA-107 (KR012992), HA-111 (KR012990), HA-113 (KR012994), HA-116 (KR012996), HA-123 (KR012995), HA-124 (KR012997), HA-126 (KR012998), HA-129 (KR012993), and HA-208 (KR012991).

DNA Vaccination with Selected Chimeric HA Constructs in Mice

Figure 3:
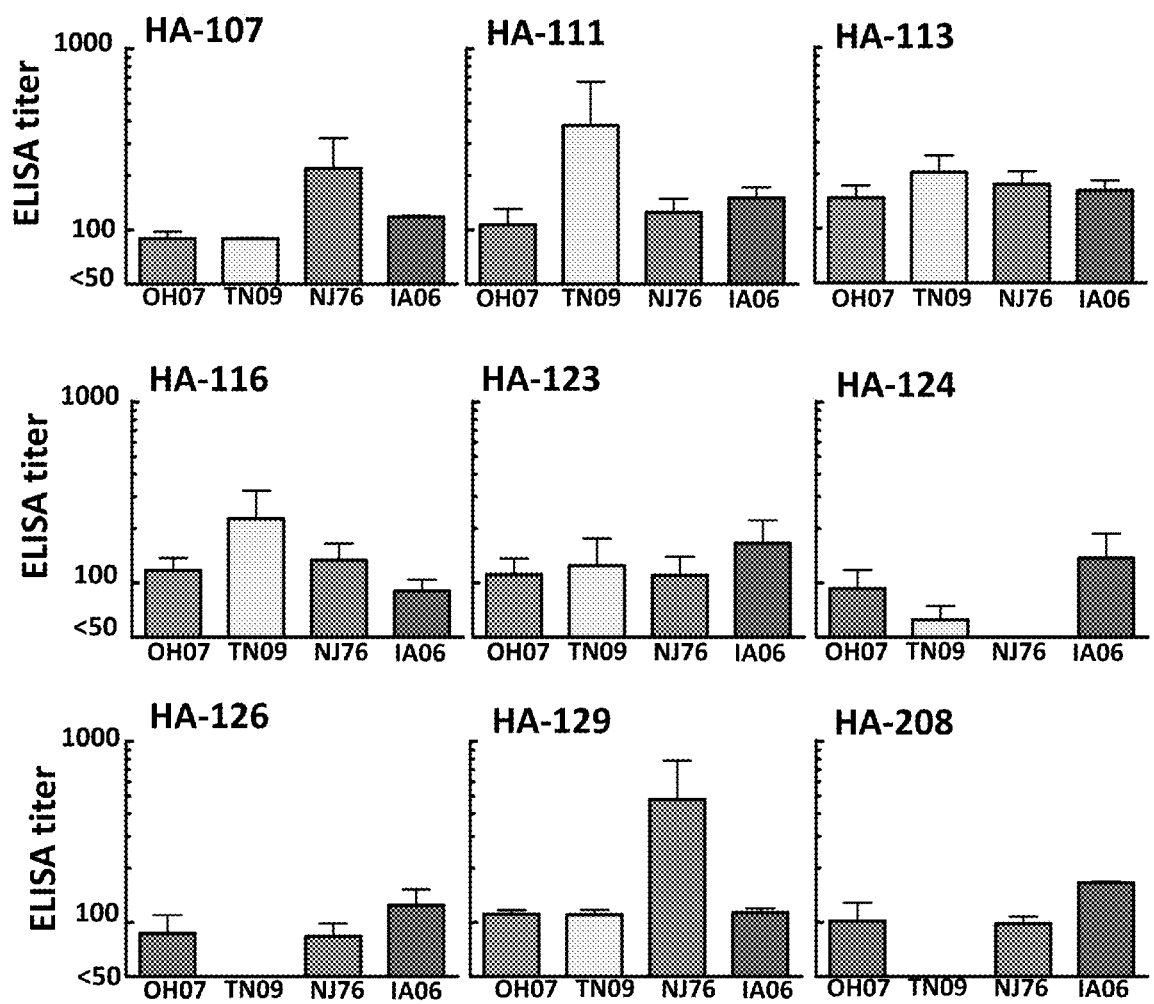
FIG. 3 shows IgG antibody response in mice immunized with plasmid DNAs expressing chimeric HA, according to certain embodiments.

After screening the HA composition, selected chimeric HAs were evaluated in mice by DNA immunization. Serum samples collected at 14 days after a third inoculation with DNA were tested for antibody response using an ELISA that incorporated parental HA-expressing viruses as antigen. The results, as seen in FIG. 3, show that IgG antibodies against all four parental viruses were detected in constructs HA-107, HA-111, HA-113, HA-116, HA-123, and HA-129. Of note, the HA-124, HA-126, and HA-208 chimeras did not induce antibodies that consistently reacted with all four parental viruses. These data demonstrate that chimeric HA constructs created using DNA shuffling method have the ability to induce broad immune responses, with some of these constructs inducing antibodies that react with all four parental HAs.

Characterization of Influenza Viruses Expressing Chimeric HA Genes

Historical approaches for influenza vaccine development utilize the natural reassortment properties of influenza viruses to express viral HA and neuraminidase (NA) genes on a PR8 master donor virus backbone. Since the majority of commercial vaccine preparations still utilize this reassortment approach, reverse genetics was used to generate viruses for candidate vaccine production. Efforts to create viruses expressing these chimeric HAs yielded only the HA-129 construct as an HA that could be expressed within a whole virus. This HA protein was expressed on both the $PR8_{LAIV}$ ($PR8_{LAIV}$-129) and the TX98 (TX98-129) backbones, which were further used for vaccination in mice and pigs, respectively.

To evaluate the in vitro properties of viruses expressing HA-129, growth characterization of $PR8_{LAIV}$-129 and TX98-129 in MDCK cells was performed. Specifically, the growth kinetics of these recombinant viruses were compared with those of either $PR8_{LAIV}$ or TX98 in MDCK cells. Supernatants were harvested from virus-infected cells at different times post-inoculation, and $TCID_{50}$ values were quantified by virus titration using separate MDCK cell monolayers. The results showed that both $PR8_{LAIV}$-129 and TX98-129 exhibit similar growth kinetics to that of $PR8_{LAIV}$ (FIG. 4A) and TX98 (FIG. 4B), indicating that virus growth was not affected by the expression of HA-129 at the surface of the virus. Similarly, in chicken eggs, both $PR8_{LAIV}$-129 and TX98-129 grew to high titers, with $TCID_{50}$ values of $10^{8.375}$ and $10^{7.5}$, respectively. Together, these data demonstrate that candidate whole virus vaccines expressing chimeric HAs can be propagated using either eggs or MDCK cells, without obvious deficiencies in growth characteristics.

Antibody Response Induced by HA-129 in Animal Models

Figure 5:
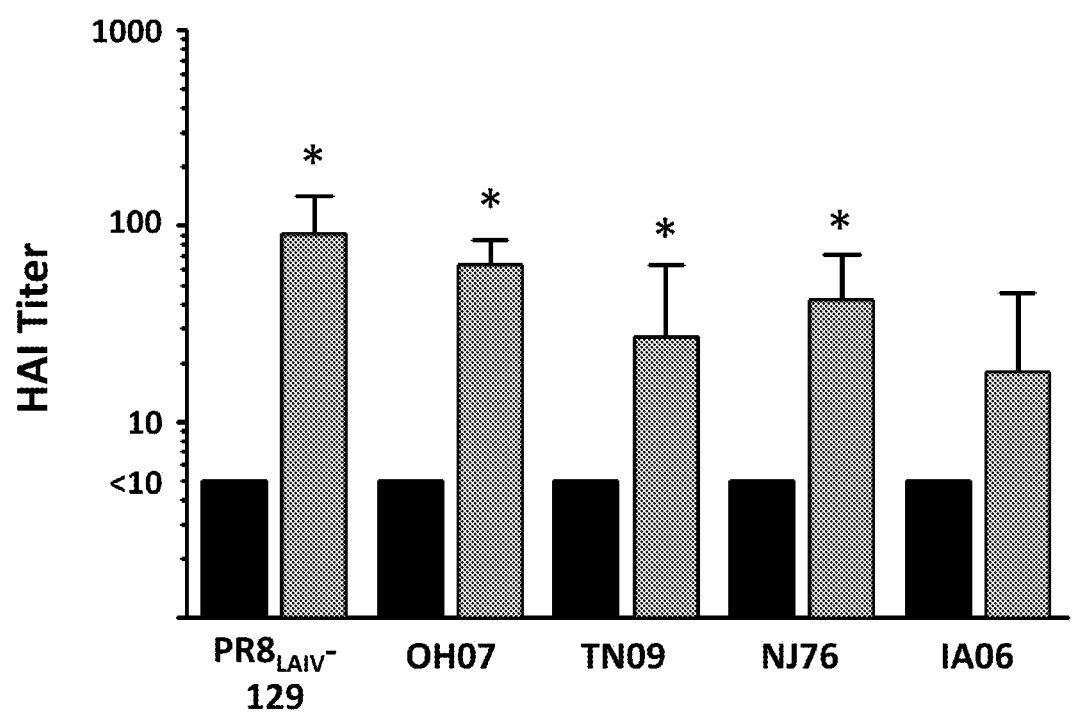
FIG. 5 shows serum antibody HAI titers from mice infected with recombinant virus $PR8_{LAIV-129}$.

Using the $PR8_{LAIV}$-129 as antigen, HAI assay results show that immune sera from mice inoculated with parental viruses broadly reacted with this chimeric HA-expressing virus (Table 2). To determine whether the $PR8_{LAIV}$-129 can be used to induce broad immune responses, mice were vaccinated with this chimeric HA-expressing virus. Specifically, mice were immunized twice with the $PR8_{LAIV}$-129, and sera were collected at 21 days post-secondary inoculation. Results from the HAI assay show that antibodies induced by the $PR8_{LAIV}$-129 react with viruses expressing each of the four parental HAs, with maximal reactivity against the virus expressing the HA-129 itself (FIG. 5). This result indicates that HA-129 is immunogenic when expressed within a whole virus, and that antibodies induced can react with all four parental HA proteins.

To determine the immunogenicity of HA-129 in pigs, pigs were immunized with the formalin-inactivated TX98-129 virus. Serum samples were collected at 14 days post-secondary immunization for analysis using both HAI and MN assays (FIG. 6). Similar to the results observed in mice, in both assays, immunized pigs developed significantly increased antibody titers ($p<0.001$) against the virus expressing HA-129, in comparison to that of serum antibody response from unvaccinated control pigs. These vaccine-induced antibodies also showed reactivity against viruses expressing parental HAs from OH07, TN09, NJ76, and IA06. To further assess the breadth of immunity induced by HA-129, additional non-parental influenza virus variants representing the major phylogenetic clades within the H1N1 influenza A virus subtype were also tested. These results show that antibodies induced after vaccination with TX98-129 were significantly increased ($p<0.05$) against a non-parental γ clade variant (A/swine/North Carolina/18161/02), two additional c clade variants (A/swine/Iowa/1/85 and A/swine/Iowa/40766/92), and a virus from the Eurasian swine lineage (A/swine/Germany/2/81) [48], as detected using both HAI and MN assays. As a comparison, serum from TX98-129-vaccinated animals did not react with the A/New Caledonia/20/99 H1N1 virus (FIG. 6), which was used here to represent the H1N1 δ clade. This result is expected, since none of the parental viruses are from δ clade.

In the Examples disclosed herein, a panel of chimeric HA constructs was created that have the ability to induce humoral immunity against four genetically divergent parental HAs. The parental viruses selected were isolated from zoonotic infections [24,49,50] and the 2009 pandemic cases [51]. They represent strains with the potential to cause future pandemics through genetic mutation. Since the molecular breeding approach mimics and accelerates the natural evolutionary pathway, in certain embodiments, these novel chimeric HA antigens induce protective immunity against the current circulating H1 viruses and have the ability to induce protective immunity against future emerging H1 strains. These findings demonstrate that an HA-based, broadly-protective vaccine could be created using this DNA shuffling method, with the added benefit of incorporating these HA constructs into conventional virus vaccines that are immunogenic in both mice and pigs. Since an influenza virus pandemic can emerge at any time, and current approaches for vaccine selection and production leave us 6-9 months away from a vaccine [11,52], we may not have a vaccine prepared to face the first wave of the next pandemic. The instantly disclosed Examples show that chimeric HA molecules can be constructed to improve the breadth of antibody responses within a single influenza A virus subtype (H1N1). This suggests that a vaccine developed using this approach would be able to limit the interspecies transmission of influenza viruses between pigs and humans and to either prevent a pandemic or significantly lessen its impact.

In the disclosed Examples, reverse genetics were used to create viruses expressing chimeric HA constructs. Recombinant viruses expressing the chimeric HA-129 on their surface ($PR8_{LAIV}$-129 and TX98-129) were successfully rescued, and the growth kinetics analysis showed that expression of the HA-129 on either the $PR8_{LAIV}$ or the TX98 genetic backbone did not affect virus propagation. The observation that these viruses could be propagated in eggs and MDCK cells provides a basis for future development of inactivated and live, attenuated influenza virus vaccine preparations using conventional, FDA-approved approaches for vaccine production [53]. The recombinant viruses rescued were used to vaccinate both mice and pigs, and they induced antibody responses against viruses expressing both parental and non-parental HAs, particularly in pigs. These data show that broad, protective immunity could be induced within the swine population using this chimeric HA construct. These results encourage our approach toward vaccinating pigs in the pre-pandemic phase, a practice that could be helpful for limiting interspecies transmission.

While not identical, the antibody response induced after DNA vaccination allowed for the screening of the HA constructs, and could also predict the breadth of humoral immunity induced by the $PR8_{LAIV}$-129 in mice and TX98-129 in pigs. This is in contrast to prior attempts to induce broad immunity within an HA subtype by vaccinating with multiple HAs simultaneously. Specifically, the results reported here demonstrate advantages of using a single HA construct, instead of multiple parental HAs delivered simultaneously, especially when attempting to deliver these HAs in the context of a $PR8_{LAIV}$ backbone [13]. Furthermore, the antibody response to $PR8_{LAIV}$-129 in mice correlated with the antibody response against TX98-129 in pigs, in which significant levels of antibodies against TN09, NJ76, OH07, and IA06 HAs were generated. In fact, based on previous reports [54,55], a HAI titer of 1:40 is considered an accepted antibody level that correlates with protective immunity in both pigs and humans, and our TX98-129-vaccinated animals developed antibodies against all four parental HAs that either met or exceeded this level. However, some of the serum samples from unvaccinated pigs generated unexpectedly high background reactivity in HAI assay, so we further analyzed the serum using MN assay to confirm that the antibodies detected by HAI were indeed neutralizing. Similar to our results from the HAI assay, we observed significant differences in neutralizing antibody titers when comparing vaccinated and unvaccinated serum samples by MN. Together, our results demonstrate that DNA vaccination can be used as a tool for screening the breadth of immunity induced by chimeric HA gene constructs, and that immunity induced by whole virus vaccine preparations expressing chimeric HAs in mice could predict the performance of similar vaccines in pigs.

It is worth noting that some other HA chimeras, including HA-107, HA-111, HA-113, HA-116, and HA-123 also induced broad antibody responses against all four parental HAs.

Turning now to the Figures, FIG. 1 shows phylogenetic comparison of swine H1 influenza hemagglutinins, including those used to create the chimeric HAs. Parental viruses included in the DNA shuffling of chimeric HA genes are identified with boxes in each phylogenic clade reported by Vincent et al. 2009 [58]. The phylogenetic tree was constructed using the Neighbor-Joining method by MEGA software version 6.0. The numbers on branches are bootstrap values from 1000 replicates.

FIG. 2 shows a schematic diagram of DNA shuffled chimeric HA gene sequences. Alignment of HA genes from chimeric constructs and parental viruses was performed using clustal W (MEGA 6) and the assignment of homology between each construct and the parental viruses was determined by a DNA shuffling alignment analysis tool (Salanto, version 2.0.2; https://bitbucket.org/benderc/salanto/wiki/Home). Different shades represent different HA gene elements from parental virus.

FIG. 3 shows the IgG antibody response in mice immunized with plasmid DNAs expressing chimeric HA. Mice (n=4) were vaccinated with plasmid DNAs of chimeric HA delivered by gene gun. Serum antibody (IgG) titers after the third vaccination were evaluated by ELISA, with samples considered positive if their initial serum $OD_{405}$ was at least three times greater than the $OD_{405}$ of negative control sera. Samples with antibody titers below the detectable limit of the assay were assigned a titer of 50 for the purpose of generating graphs. Bars show mean values, and error bars indicate standard deviation.

Figure 4A:
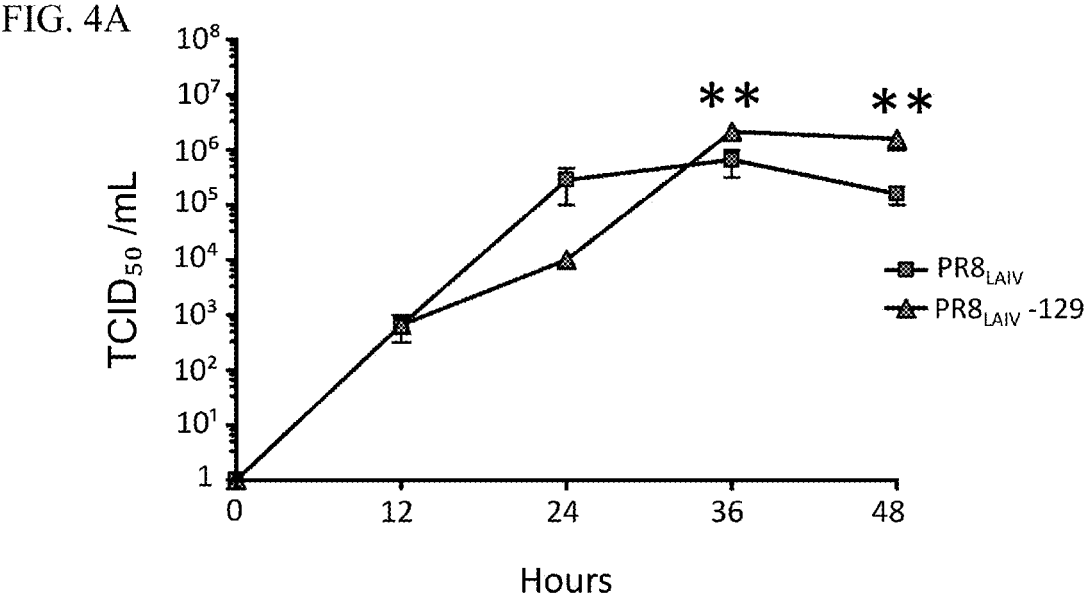
FIG. 4A and FIG. 4B show comparison of growth kinetics of wild type virus with recombinant viruses expressing HA-129.
Figure 4B:
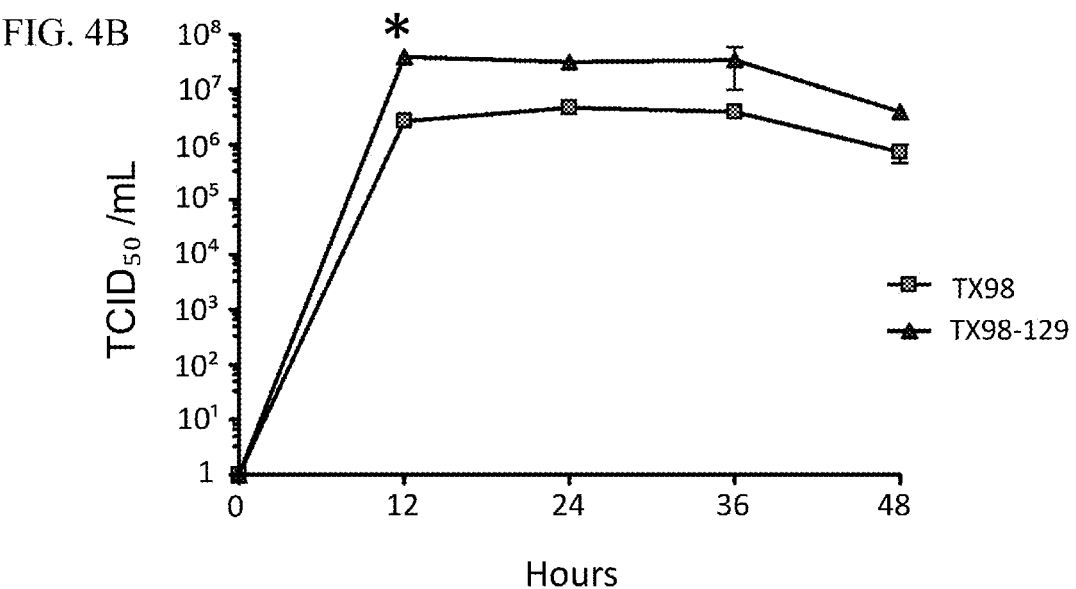

FIGS. 4a and 4b show the comparison of growth kinetics of wild type virus with recombinant viruses expressing HA-129. (A) MDCK cells were inoculated with a 0.01 MOI of either wild type virus $PR8_{LAIV}$ or recombinant virus $PR8_{LAIV}$-129. (B) MDCK cells were infected with wild type virus A/swine/Texas/4199-2/98 (TX98) or recombinant virus TX98-129. At the 12-hour time points indicated, cell culture supernatants were collected and titers were determined by $TCID_{50}$ quantitation. Error bars represent SEM, with significance between paired viruses at time points denoted by asterisks (*p<0.05 and **p<0.01 using two-way repeated measures ANOVA with Bonferroni post-test).

FIG. 5 shows serum antibody HAI titers from mice infected with recombinant virus $PR8_{LAIV}$-129. BALB/c mice (n=7) were vaccinated intranasally with $PR8_{LAIV}$-129. Serum antibody levels were analyzed using the HAI assay against the parental viruses and $PR8_{LAIV}$-129. HAI titers are defined as the reciprocal of the final serum dilution where inhibition of hemagglutination was observed. Serum samples with a titer below the detectable limit of the assay (initial serum dilution of 1:10) were assigned a value of 5 for graphical representation and statistical analyses. HAI titers from vaccinated (grey bars) and unvaccinated (black bars) groups are presented for each HA tested ($PR8_{LAIV}$-129, OH07, TN09, NJ76, and IA06). Reactivity of antibodies induced by $PR8_{LAIV}$-129 from vaccinated mice was compared with that of unvaccinated mice using Mann Whitney nonparametric test (*p<0.05). Bars represent mean value with error bars indicating standard deviation.

Figure 6A:
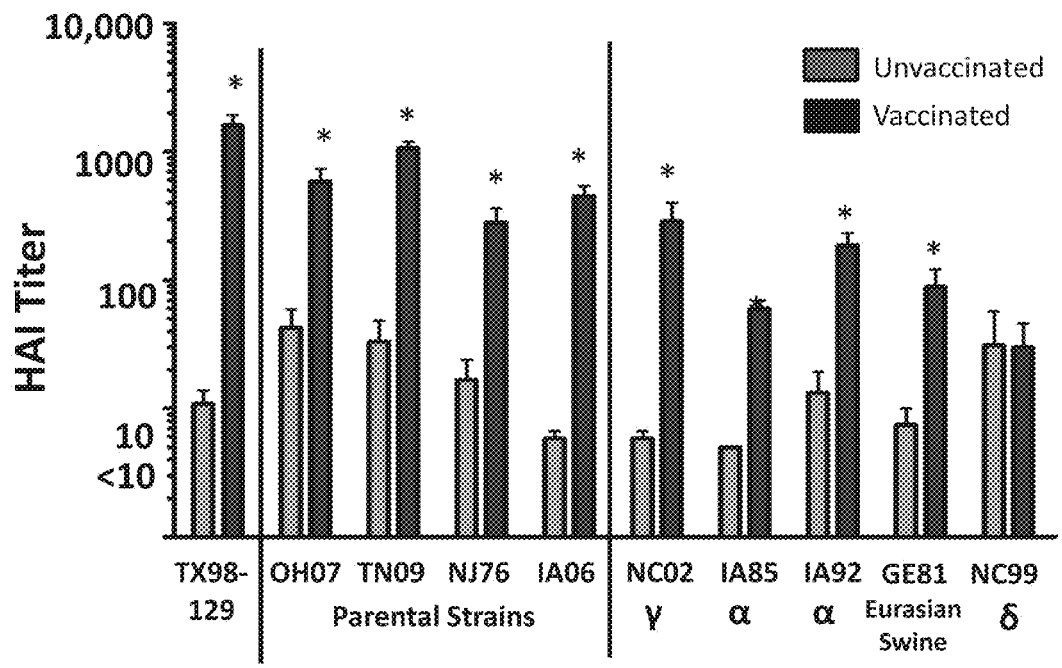
FIG. 6A and FIG. 6B show antibody reactivity against viruses expressing parental or non-parental HAs using serum samples from pigs immunized with the TX98-129 IIV.
Figure 6B:
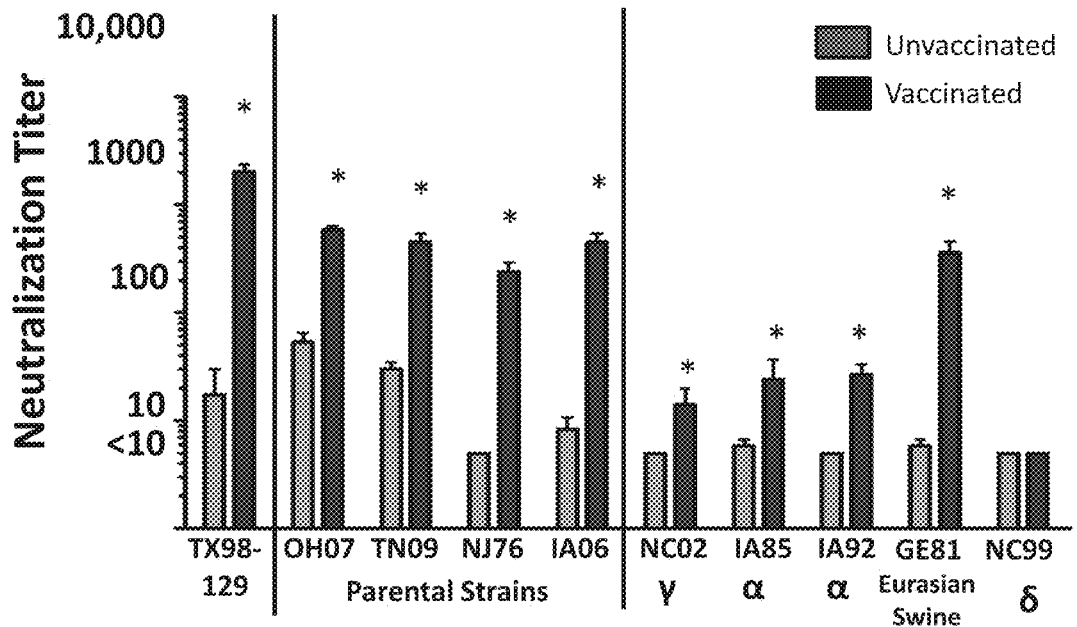

FIGS. 6a and 6b show antibody reactivity against viruses expressing parental or non-parental HAs using serum samples from pigs immunized with the TX98-129 IIV. Sera were collected at 28 days after inoculation of pigs with the TX98-129 IIV. (A) Serum antibody HAI assay. HAI titers are defined as the reciprocal of the final serum dilution where inhibition of hemagglutination was observed. (B) Serum antibody microneutralization (MN) assay. MN titers are defined as the reciprocal of the final serum dilution where $OD_{490}$ was below 50% of positive control wells, using 100 $TCID_{50}$ virus inoculum (confirmed by back-titration). Serum samples with a titer below the detectable limit of the assay (initial serum dilution of 1:10) were assigned a value of 5 for graphical representation and statistical analyses. Viruses expressing non-parental HA proteins are abbreviated (A/North Carolina/18161/2002: NC02; A/sw/Iowa/1/1985: IA85; A/sw/Iowa/40766/1992: IA92; A/sw/Germany/2/1981: GE81; A/New Caledonia/20/99: NC99) and shown with clade representation. Significance between vaccinated vs. unvaccinated for all viruses using a Mann Whitney nonparametric test (*p<0.05).

Figure 7:
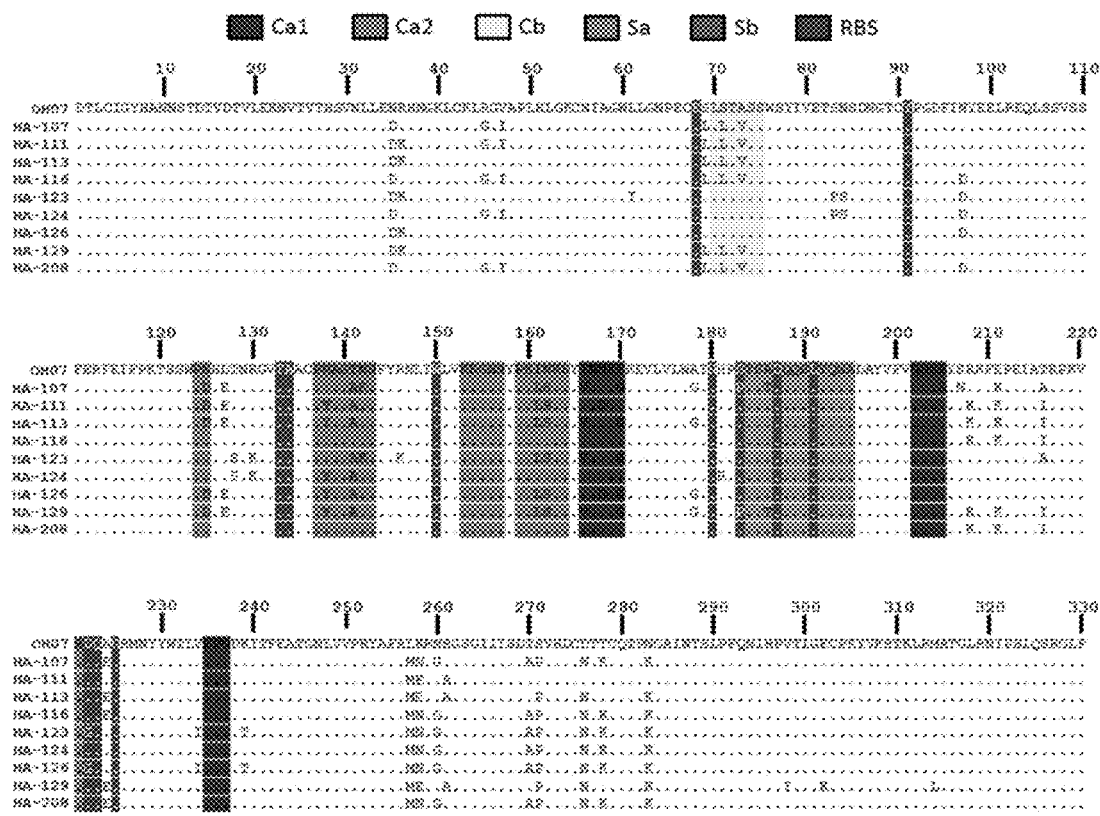
FIG. 7 shows alignment of the chimeric HAs with A/Ohio/01/2007 (H1N1) (SEQ ID NO 11).

FIG. 7 shows a comparison of antigenic sites of shuffled chimeric HA sequences with that of a parental HA. Amino acid alignment of the HA protein from A/Ohio/01/2007 (H1N1) with chimeric HAs. Antigenic sites Ca1, Ca2, Cb, Sa, Sb, and the receptor binding site (RBS) were boxed and shaded.

Figure 8:
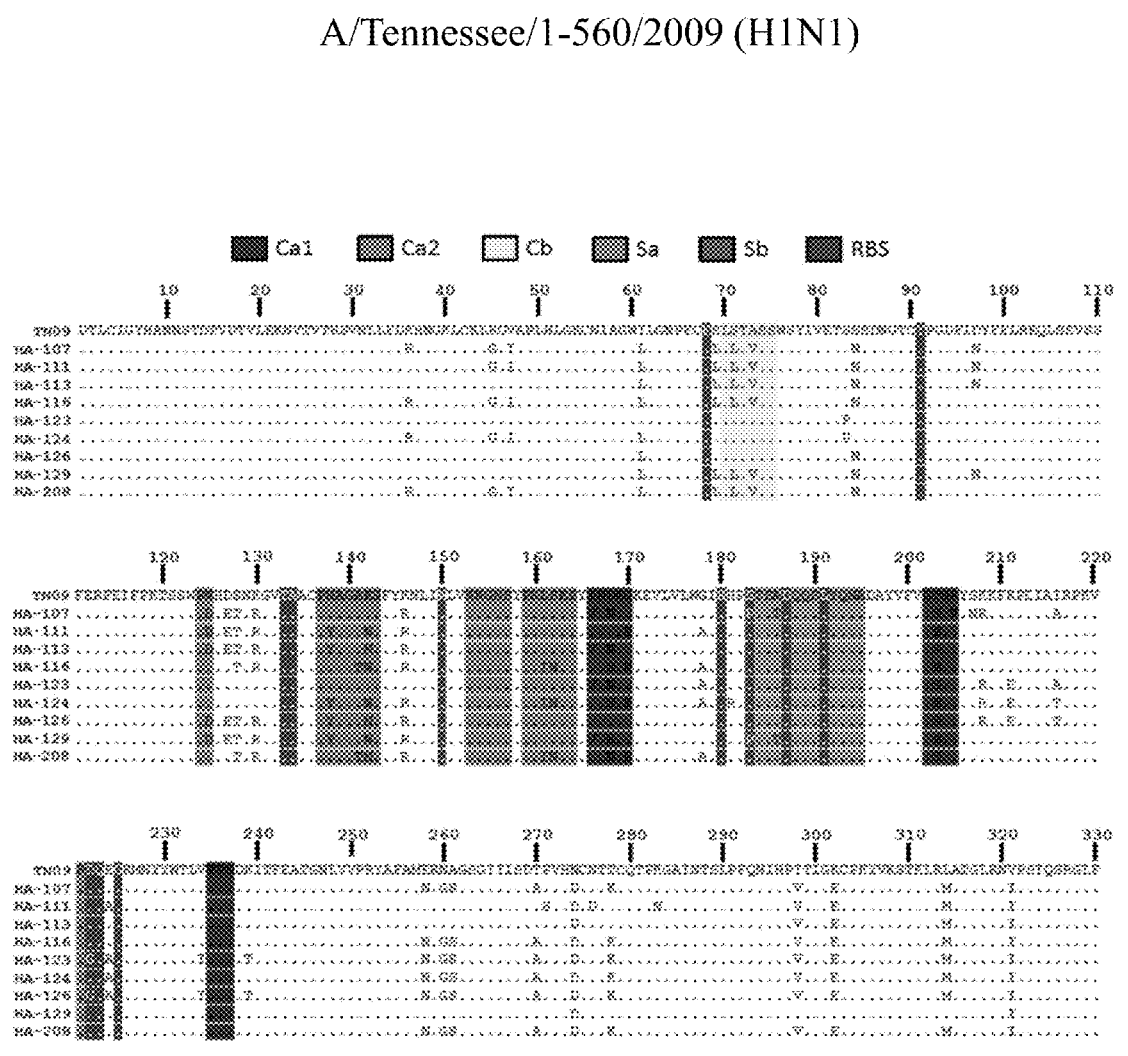

FIG. 8 shows a comparison of antigenic sites of shuffled chimeric HA sequences with that of a parental HA. Amino acid alignment of the HA protein from A/Tennessee/1-560/2009 (H1N1) with chimeric HAs. Antigenic sites Ca1, Ca2, Cb, Sa, Sb, and the receptor binding site (RBS) were boxed and shaded.

Figure 9:
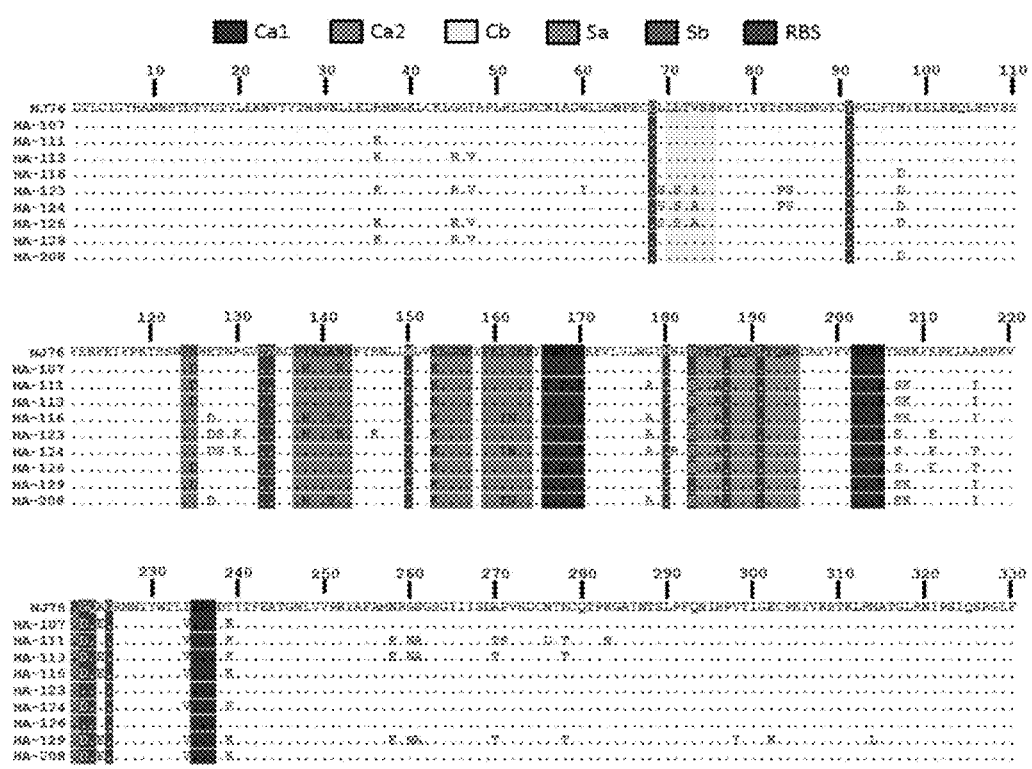
FIG. 9 shows alignment of the chimeric HAs with A/New Jersey/8/76 (H1N1) (SEQ ID NO 12).

FIG. 9 shows a comparison of antigenic sites of shuffled chimeric HA sequences with that of a parental HA. Amino acid alignment of the HA protein from A/New Jersey/8/76 (H1N1) with chimeric HAs. Antigenic sites Ca1, Ca2, Cb, Sa, Sb, and the receptor binding site (RBS) were boxed and shaded.

Figure 10:
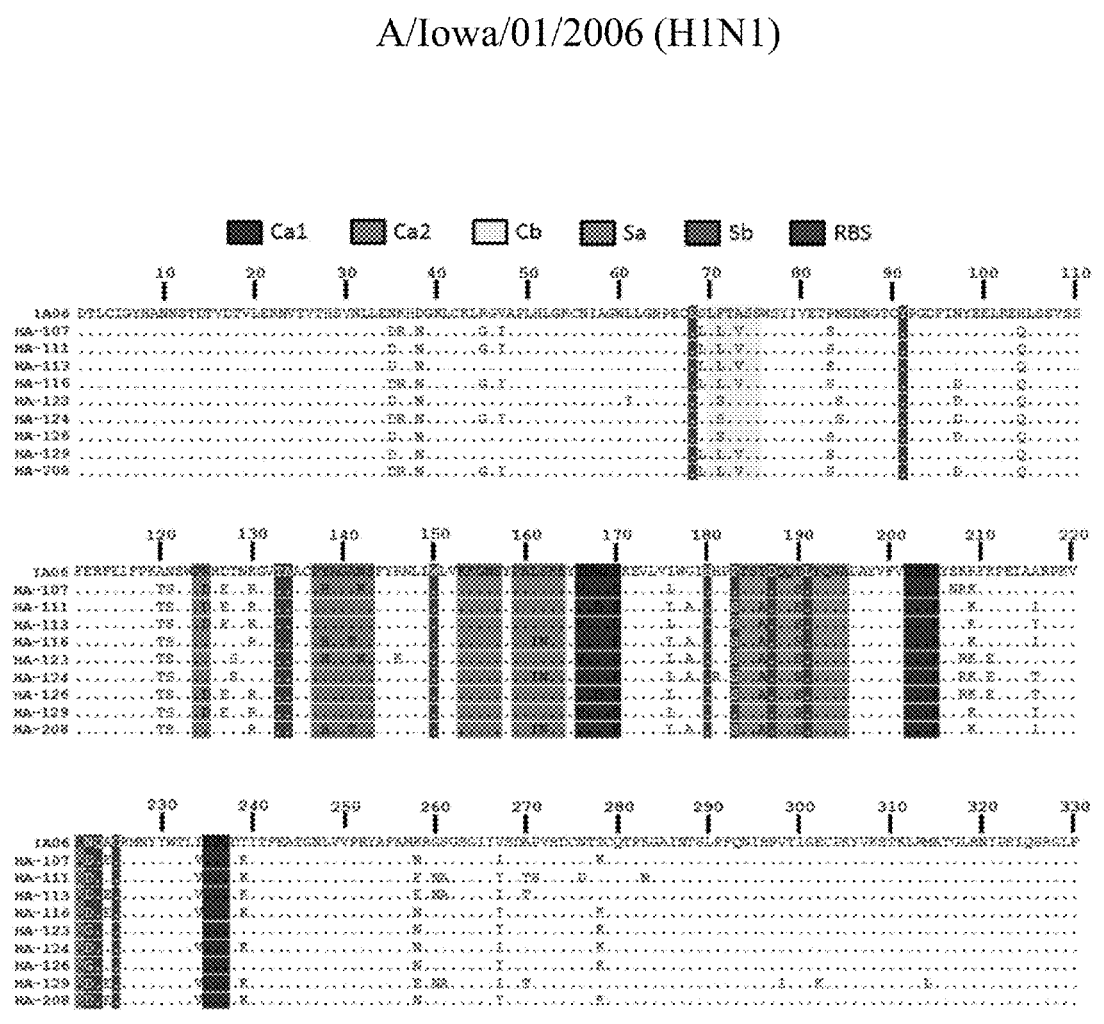

FIG. 10 shows a comparison of antigenic sites of shuffled chimeric HA sequences with that of a parental HA. Amino acid alignment of the HA protein from A/Iowa/01/2006 (H1N1) with chimeric HAs. Antigenic sites Ca1, Ca2, Cb, Sa, Sb, and the receptor binding site (RBS) were boxed and shaded.

TABLE 1

Virus Names, Subtypes and Accession Numbers Included in Phylogenetic Tree

| Virus Name | Accession |
| --- | --- |
| A/Ohio/01/2007(H1N1) | FJ986620 |
| A/swine/Minnesota/03025/2010(H1N1) | HM570051 |

TABLE 1-continued

Virus Names, Subtypes and Accession Numbers Included in Phylogenetic Tree

| Virus Name | Accession |
|---|---|
| A/swine/Illinois/03037/2010(H1N1) | HM754221 |
| A/Swine/Ohio/891/01(H1N2) | AF455675 |
| A/Tennessee/1-560/2009(H1N1) | CY040457 |
| A/New Jersey/8/1976(H1N1) | CY130118 |
| A/Texas/05/2009(H1N1) | FJ966959 |
| A/California/04/2009(H1N1) | FJ966082 |
| A/Iowa/01/2006(H1N1) | FJ986618 |
| A/swine/Kentucky/02086/2008(H1N1) | HM461786 |
| A/swine/Iowa/1973(H1N1) | EU139826 |
| A/swine/Iowa/2/1987(H1N1) | CY028171 |
| A/swine/Ontario/53518/03(H1N1) | DQ280219 |
| A/swine/Minnesota/02053/2008(H1N1) | CY099119 |
| A/swine/Iowa/1/1985(H1N1) | CY022317 |
| A/Swine/North Carolina/98225/01(H1N2) | AF455676 |
| A/Swine/Iowa/930/01(H1N2) | AF455679 |
| A/swine/MN/48683/2002(H1N1) | HM125974 |
| A/swine/North Carolina/18161/2002(H1N1) | CY098516 |
| A/swine/Germany/2/1981(H1N1) | Z30276 |
| A/swine/Tennessee/49/1977(H1N1) | CY022133 |
| A/swine/Tennessee/8/1978(H1N1) | CY027523 |
| A/swine/Netherlands/12/85(H1N1) | AF091317 |
| A/South Carolina/1/18 (H1N1) | AF117241 |
| A/swine/Iowa/15/1930(H1N1) | EU139823 |
| A/swine/Colorado/1/1977(H3N2) | CY009300 |
| A/swine/Iowa/40766/1992(H1N1) | KP788773 |

TABLE 2

Antibody cross reactivity in sera from mice infected with recombinant viruses expressing parental or chimeric HA protein

| | Post-Infection Sera | | | |
|---|---|---|---|---|
| Virus Isolate | OH07 | IA06 | NJ76 | TN09 |
| PR8-OH07 | 1280 | 320 | *< | 80 |
| PR8-IA06 | < | 5120** | 320 | 80 |
| PR8-NJ76 | < | 320 | 1280 | < |
| PR8-TN09 | 40 | 160 | < | 320 |
| PR8$_{LAIV}$-129 | 80 | 320 | 160 | 320 |

*<: HI titer less than 1:40.
**A four-fold difference in antibody reactivity represents an acceptable antigenic distance for vaccine selection [41].

TABLE 3

Antigenic distance between selected H1 HA proteins.

| | Antigenic distance | | | |
|---|---|---|---|---|
| Virus Isolate | OH07 | IA06 | NJ76 | TN09 |
| PR8-OH07 | NA* | 136 | 256 | 18 |
| PR8-IA06 | 136** | NA | 10 | 18 |
| PR8-NJ76 | 256 | 18 | NA | 160 |
| PR8-TN09 | 18 | 18 | 160 | NA |

*NA: Not Applicable.
**A four-fold difference represents an acceptable antigenic distance for vaccine selection [41].

Although the present invention has been described with reference to preferred embodiments, persons skilled in the art will recognize that changes may be made in form and detail without departing from the spirit and scope of the invention.

REFERENCES

1. Webster R G, Bean W J, Gorman O T, Chambers T M, Kawaoka Y (1992) Evolution and ecology of influenza A viruses. Microbiol Rev 56: 152-179.
2. Klimov A, Simonsen L, Fukuda K, Cox N (1999) Surveillance and impact of influenza in the United States. Vaccine 17 Suppl 1: S42-S46.
3. Richt J A, Lekcharoensuk P, Lager K M, Vincent A L, Loiacono C M, Janke B H, Wu W H, Yoon K J, Webby R J, Solorzano A, Garcia-Sastre A (2006) Vaccination of pigs against swine influenza viruses by using an NS1-truncated modified live-virus vaccine. J Virol 80: 11009-11018.
4. Hause B M, Stine D L, Sheng Z, Wang Z, Chakravarty S, Simonson R R, Li F (2012) Migration of the swine influenza virus delta-cluster hemagglutinin N-linked glycosylation site from N142 to N144 results in loss of antibody cross-reactivity. Clin Vaccine Immunol 19: 1457-1464. CVI.00096-12 [pii]; 10. 1128/CVI.00096-12 [doi].
5. Osterholm M T, Kelley N S, Sommer A, Belongia E A (2012) Efficacy and effectiveness of influenza vaccines: a systematic review and meta-analysis. Lancet Infect Dis 12: 36-44.
6. Nichol K L (2008) Efficacy and effectiveness of influenza vaccination. Vaccine 26 Suppl 4: D17-D22.
7. Kilbourne E D (2006) Influenza pandemics of the 20th century. Emerg Infect Dis 12: 9-14.
8. Webby R J, Webster R G (2003) Are we ready for pandemic influenza? Science 302: 1519-1522.
9. Vijaykrishna D, Poon L L, Zhu H C, Ma S K, Li O T, Cheung C L, Smith G J, Peiris J S, Guan Y (2010) Reassortment of pandemic H1N1/2009 influenza A virus in swine. Science 328: 1529.
10. Meiklejohn G (1983) Viral respiratory disease at Lowry Air Force Base in Denver, 1952-1982. J Infect Dis 148: 775-784.
11. Gerdil C (2003) The annual production cycle for influenza vaccine. Vaccine 21: 1776-1779.
12. Schultz-Cherry S, Olsen C W, Easterday B C (2012) History of Swine Influenza. Curr Top Microbiol Immunol.
13. Huber V C, Thomas P G, McCullers J A (2009) A multi-valent vaccine approach that elicits broad immunity within an influenza subtype. Vaccine 27: 1192-1200.
14. Zhao G, Hortsch M (1998) The analysis of genomic structures in the L1 family of cell adhesion molecules provides no evidence for exon shuffling events after the separation of arthropod and chordate lineages. Gene 215: 47-55. S0378-1119(98)00273-X [pii].
15. Ness J E, Welch M, Giver L, Bueno M, Cherry J R, Borchert T V, Stemmer W P, Minshull J (1999) DNA shuffling of subgenomic sequences of subtilisin. Nat Biotechnol 17: 893-896. 10.1038/12884 [doi].
16. Ness J E, Kim S, Gottman A, Pak R, Krebber A, Borchert T V, Govindarajan S, Mundorff E C, Minshull J (2002) Synthetic shuffling expands functional protein diversity by allowing amino acids to recombine independently. Nat Biotechnol 20: 1251-1255. 10.1038/nbt754 [doi]; nbt754 [pii].
17. Chang C C, Chen T T, Cox B W, Dawes G N, Stemmer W P, Punnonen J, Patten P A (1999) Evolution of a cytokine using DNA family shuffling. Nat Biotechnol 17: 793-797. 10.1038/11737 [doi].
18. Burgers W A, van Harmelen J H, Shephard E, Adams C, Mgwebi T, Bourn W, Hanke T, Williamson A L, Williamson C (2006) Design and preclinical evaluation of a 18. multigene human immunodeficiency virus type 1 subtype C DNA vaccine for clinical trial. J Gen Virol 87: 399-410. 87/2/399 [pii]; 10.1099/vir.0.81379-0 [doi].
19. Callison S, Hilt D, Jackwood M (2005) Using DNA shuffling to create novel infectious bronchitis virus S1 genes: implications for S1 gene recombination. Virus Genes 31: 5-11. 10.1007/s 1262-004-2194-3 [doi].
20. Osen W, Peiler T, Ohlschlager P, Caldeira S, Faath S, Michel N, Muller M, Tommasino M, Jochmus I, Gissmann L (2001) A DNA vaccine based on a shuffled E7 oncogene of the human papillomavirus type 16 (HPV 16) induces E7-specific cytotoxic T cells but lacks transforming activity. Vaccine 19: 4276-4286. S0264-410X(01) 00154-2 [pii].
21. Raviprakash K, Apt D, Brinkman A, Skinner C, Yang S, Dawes G, Ewing D, Wu S J, Bass S, Punnonen J, Porter K (2006) A chimeric tetravalent dengue DNA vaccine elicits neutralizing antibody to all four virus serotypes in rhesus macaques. Virology 353: 166-173.
22. Apt D, Raviprakash K, Brinkman A, Semyonov A, Yang S, Skinner C, Diehl L, Lyons R, Porter K, Punnonen J (2006) Tetravalent neutralizing antibody response against four dengue serotypes by a single chimeric dengue envelope antigen. Vaccine 24: 335-344.
23. Crameri A, Raillard S A, Bermudez E, Stemmer W P (1998) DNA shuffling of a family of genes from diverse species accelerates directed evolution. Nature 391: 288-291. 10.1038/34663 [doi].
24. Yassine H M, Khatri M, Zhang Y J, Lee C W, Byrum B A, O'Quin J, Smith K A, Saif Y M (2009) Characterization of triple reassortant H1N1 influenza A viruses from swine in Ohio. Vet Microbiol 139: 132-139.
25. Lorusso A, Vincent A L, Harland M L, Alt D, Bayles D O, Swenson S L, Gramer M R, Russell C A, Smith D J, Lager K M, Lewis N S (2011) Genetic and antigenic characterization of H1 influenza viruses from United States swine from 2008. J Gen Virol 92: 919-930.
26. Hoffmann E, Neumann G, Kawaoka Y, Hobom G, Webster R G (2000) A DNA transfection system for generation of influenza A virus from eight plasmids. Proc Natl Acad Sci USA 97: 6108-6113.
27. Hoffmann E, Krauss S, Perez D, Webby R, Webster R G (2002) Eight-plasmid system for rapid generation of influenza virus vaccines. Vaccine 20: 3165-3170.
28. Hoffmann E, Webster R G (2000) Unidirectional RNA polymerase I-polymerase II transcription system for the generation of influenza A virus from eight plasmids. J Gen Virol 81: 2843-2847.
29. Soong N W, Nomura L, Pekrun K, Reed M, Sheppard L, Dawes G, Stemmer W P (2000) Molecular breeding of viruses. Nat Genet 25: 436-439.
30. Kilbourne E D (1969) Future influenza vaccines and the use of genetic recombinants. Bull World Health Organ 41: 643-645.
31. Kilbourne E D, Schulman J L, Schild G C, Schloer G, Swanson J, Bucher D (1971) Related studies of a recombinant influenza-virus vaccine. I. Derivation and characterization of virus and vaccine. J Infect Dis 124: 449-462.
32. Vincent A L, Ma W, Lager K M, Richt J A, Janke B H, Sandbulte M R, Gauger P C, Loving C L, Webby R J, Garcia-Sastre A (2012) Live attenuated influenza vaccine provides superior protection from heterologous infection in pigs with maternal antibodies without inducing vaccine-associated enhanced respiratory disease. J Virol 86: 10597-10605. JVI.01439-12 [pii]; 10.1128/JVI.01439-12 [doi].
33. Jin H, Zhou H, Lu B, Kemble G (2004) Imparting temperature sensitivity and attenuation in ferrets to A/Puerto Rico/8/34 influenza virus by transferring the genetic signature for temperature sensitivity from cold-adapted A/Ann Arbor/6/60. J Virol 78: 995-998.
34. Huber V C, McCullers J A (2006) Live attenuated influenza vaccine is safe and immunogenic in immunocompromised ferrets. J Infect Dis 193: 677-684.
35. Reed L J, Muench H (1938) A simple method of estimating 50% endpoints. Am J Hyg 27: 493-497.
36. Huber V C, McKeon R M, Brackin M N, Miller L A, Keating R, Brown S A, Makarova N, Perez D R, Macdonald G H, McCullers J A (2006) Distinct contributions of vaccine-induced immunoglobulin G1 (IgG1) and IgG2a antibodies to protective immunity against influenza. Clin Vaccine Immunol 13: 981-990.
37. Cwach K T, Sandbulte H R, Klonoski J M, Huber V C (2012) Contribution of murine innate serum inhibitors toward interference within influenza virus immune assays. Influenza Other Respi Viruses 6: 127-135.
38. Rowe T, Abernathy R A, Hu-Primmer J, Thompson W W, Lu X, Lim W, Fukuda K, Cox N J, Katz J M (1999) Detection of antibody to avian influenza A (H5N1) virus in human serum by using a combination of serologic assays. J Clin Microbiol 37: 937-943.
39. World Health Organization (2002) WHO Manual on Animal Influenza Diagnosis and Surveillance. In: Webster R G, Cox N, Stohr K, editors. World Health Organization. pp. 1-135.
40. Chaussee M S, Sandbulte H R, Schuneman M J, DePaula F P, Addengast L A, Schlenker E H, Huber V C (2011) Inactivated and live, attenuated influenza vaccines protect mice against influenza: *Streptococcus pyogenes* superinfections. Vaccine 29: 3773-3781. S0264-410X(11) 00383-5 [pii]; 10.1016/j.vaccine.2011.03.031 [doi].
41. Cai Z, Zhang T, Wan X F (2012) Antigenic distance measurements for seasonal influenza vaccine selection. Vaccine 30: 448-453.
42. Schurmann N, Trabuco L G, Bender C, Russell R B, Grimm D (2013) Molecular dissection of human Argonaute proteins by DNA shuffling. Nat Struct Mol Biol 20: 818-826. nsmb.2607 [pii]; 10.1038/nsmb.2607 [doi].
43. Caton A J, Brownlee G G, Yewdell J W, Gerhard W (1982) The antigenic structure of the influenza virus A/PR/8/34 hemagglutinin (H1 subtype). Cell 31: 417-427.
44. Hensley S E, Yewdell J W (2009) Que sera, sera: evolution of the swine H1N1 influenza A virus. Expert Rev Anti Infect Ther 7: 763-768.
45. Almansour I, Chen H, Wang S, Lu S (2013) Cross reactivity of serum antibody responses elicited by DNA vaccines expressing H A antigens from H1N1 subtype influenza vaccines in the past 30 years. Hum Vaccin Immunother 9: 2049-2059. 25735 [pii]; 10.4161/ hv.25735 [doi].
46. Fulvini A A, Ramanunninair M, Le J, Pokorny B A, Arroyo J M, Silverman J, Devis R, Bucher D (2011) Gene constellation of influenza a virus reassortants with high growth phenotype prepared as seed candidates for vaccine production. PLoS One 6: e20823.
47. Ramanunninair M, Le J, Onodera S, Fulvini A A, Pokorny B A, Silverman J, Devis R, Arroyo J M, He Y, Boyne A, Bera J, Halpin R, Hine E, Spiro D J, Bucher D (2013) Molecular signature of high yield (growth) influenza a virus reassortants prepared as candidate vaccine seeds. PLoS One 8: e65955. 10.1371/journal. pone.0065955 [doi]; PONE-D-12-25674 [pii].

48. Brown I H, Ludwig S, Olsen C W, Hannoun C, Scholtissek C, Hinshaw V S, Harris P A, McCauley J W, Strong I, Alexander D J (1997) Antigenic and genetic analyses of H1N1 influenza A viruses from European pigs. J Gen Virol 78 (Pt 3): 553-562.
49. Lorusso A, Vincent A L, Harland M L, Alt D, Bayles D O, Swenson S L, Gramer M R, Russell C A, Smith D J, Lager K M, Lewis N S (2011) Genetic and antigenic characterization of H1 influenza viruses from United States swine from 2008. J Gen Virol 92: 919-930. vir.0.027557-0 [pii]; 10.1099/vir.0.027557-0 [doi].
50. Shinde V, Bridges C B, Uyeki T M, Shu B, Balish A, Xu X, Lindstrom S, Gubareva L V, Deyde V, Garten R J, Harris M, Gerber S, Vagasky S, Smith F, Pascoe N, Martin K, Dufficy D, Ritger K, Conover C, Quinlisk P, Klimov A, Bresee J S, Finelli L (2009) Triple-reassortant swine influenza A (H1) in humans in the United States, 2005-2009. N Engl J Med 360: 2616-2625.
51. Rowe T, Leon A J, Crevar C J, Carter D M, Xu L, Ran L, Fang Y, Cameron C M, Cameron M J, Banner D, Ng D C, Ran R, Weirback H K, Wiley C A, Kelvin D J, Ross T M (2010) Modeling host responses in ferrets during A/California/07/2009 influenza infection. Virology 401: 257-265.
52. Robertson J S, Nicolson C, Harvey R, Johnson R, Major D, Guilfoyle K, Roseby S, Newman R, Collin R, Wallis C, Engelhardt O G, Wood J M, Le J, Manojkumar R, Pokorny B A, Silverman J, Devis R, Bucher D, Verity E, Agius C, Camuglia S, Ong C, Rockman S, Curtis A, Schoofs P, Zoueva O, Xie H, Li X, Lin Z, Ye Z, Chen L M, O'Neill E, Balish A, Lipatov A S, Guo Z, Isakova I, Davis C T, Rivailler P, Gustin K M, Belser J A, Maines T R, Tumpey T M, Xu X, Katz J M, Klimov A, Cox N J, Donis R O (2011) The development of vaccine viruses against pandemic A(H1N1) influenza. Vaccine 29: 1836-1843.
53. Fiore A E, Uyeki T M, Broder K, Finelli L, Euler G L, Singleton J A, Iskander J K, Wortley P M, Shay D K, Bresee J S, Cox N J (2010) Prevention and control of influenza with vaccines: recommendations of the Advisory Committee on Immunization Practices (ACIP), 2010. MMWR Recomm Rep 59: 1-62.
54. Hobson D, Curry R L, Beare A S, Ward-Gardner A (1972) The role of serum haemagglutination-inhibiting antibody in protection against challenge infection with influenza A2 and B viruses. J Hyg (Lond) 70: 767-777.
55. Black S, Nicolay U, Vesikari T, Knuf M, Del G G, Della C G, Tsai T, Clemens R, Rappuoli R (2011) Hemagglutination inhibition antibody titers as a correlate of protection for inactivated influenza vaccines in children. Pediatr Infect Dis J 30: 1081-1085.
56. 2013) Prevention and control of influenza with vaccines: interim recommendations of the Advisory Committee on Immunization Practices (ACIP), 2013. MMWR Morb Mortal Wkly Rep 62: 356. mm6218a3 [pii].
57. Flannery B, Clippard J, Zimmerman R K, Nowalk M P, Jackson M L, Jackson L A, Monto A S, Petrie J G, McLean H Q, Belongia E A, Gaglani M, Berman L, Foust A, Sessions W, Thaker S N, Spencer S, Fry A M (2015) Early estimates of seasonal influenza vaccine effectiveness—United States, january 2015. MMWR Morb Mortal Wkly Rep 64: 10-15. mm6401a4 [pii].
58. Vincent A L, Ma W, Lager K M, Gramer M R, Richt J A, Janke B H (2009) Characterization of a newly emerged genetic cluster of H1N1 and H1N2 swine influenza virus in the United States. Virus Genes.

```
                  SEQUENCE LISTING

SEQ ID NO: 1  (HA:107_Chimeric_H1N1|segment4:HA)
DTLC1GYHANNSTDTVDTVLEKNVTVTHSVNLLEDRHNGKLCKLGGIAPL
HLGKCNIAGWLLGNPECELLLTVSSWSYIVETSNSDNGTCYPGDFINYEE
LREQLSSVSSFERFEIFPKTSSWPDHETNRGVTAACPHAGAKSFYRNLIW
LVKKGNSYPKLSKSYVNNKGKEVLVLWGIHHPPTSTDQQSLYQNADAYVF
VGSSKYNRKFKPEIAARPKVRDQEGRMNYYWTLVEPGDKITFEATGNLVV
PRYAFAMNRGSGSGIIISDAPVHDCNTKCQTPKGAINTSLPFQNIHP
VTIGECPKYVKSTKLRMATGLRNIPSIQSRGLF SEQ ID NO: 2  (HA:111_Chimeric_H1N1|segment4:HA)
DTLC1GYHANNSTDTVDTVLEKNVTVTHSVNLLEDKHNGKLCKLGGIAPL
HLGKCNIAGWLLGNPECELLLTVSSWSYIVETSNSDNGTCYPGDFINYEE
LREQLSSVSSFERFEIFPKTSSWPDHETNRGVTAACPYAGANSFYRNLIW
LVKKGNSYPKLSKSY1NDKEKEVLVLWAIHHPSTSADQQSLYQNADAYVF
VGSSRYSKKFKPEIAIRPKVRDQAGRMNYYWTLVEPGDKITFEATGNLVV
PRYAFAMERNAGSGIIISDTSVHDCDTTCQTPNGAINTSLPFQNIHPVTI
GECPKYVKSTKLRMATGLRNIPSIQSRGLF SEQ ID NO: 3  (HA:113_Chimeric_H1N1|segment4:HA)
DTLCIGYHANNSTDTVDTVLEKNVTVTHSVNLLEDKHNGKLCKLRGVAPL
HLGKCNIAGWLLGNPECELLLTVSSWSYIVETSNSDNGTCYPGDFINYEE
LREQLSSVSSFERFEIFPKTSSWPDHETNRGVTAACPYAGANSFYRNLIW
LVKKGNSYPKLSKSYVNNKGKEVLVLWGIHHPSTSADQQSLYQNADAYVF
VGSSRYSKKFKPEIAIRPKVRDQEGRMNYYWTLVEPGDKITFEATGNLVV
PRYAFAMERNAGSGIIISDTPVHDCNTTCQTPKGAINTSLPFQNIHPVTI
GECPKYVKSTKLRMATGLRNIPSIQSRGLF SEQ ID NO: 4  (HA:116_Chimeric_H1N1|segment4:HA)
DTLCIGYHANNSTDTVDTVLEKNVTVTHSVNLLEDRHNGKLCKLGGIAPL
HLGKCNIAGWLLGNPECELLLTVSSWSYIVETSNSDNGTCYPGDFIDYEE
LREQLSSVSSFERFEIFPKTSSWPNHDTNRGVTAACPHAGTNSFYRNLIW
LVKKGNSYPKINKSYINNKEKEVLVLWAIHHPSTSADQQSLYQNADAYVF
VGSSRYSKKFKPEIAIRPKVRDQEGRMNYYWTLVEPGDKITFEATGNLVV
PRYAFAMNRGSGSGIIISDAPVHDCNTKCQTPKGAINTSLPFQNIHPVTI
GECPKYVKSTKLRMATGLRNIPSIQSRGLF SEQ ID NO: 5  (HA:123_Chimeric_H1N1|segment4:HA)
DTLCIGYHANNSTDTVDTVLEKNVTVTHSVNLLEDKHNGKLCKLRGVAPL
HLGKCNIAGWILGNPECESLSTASSWSYIVETPSSDNGTCYPGDFIDYEE
LREQLSSVSSFERFEIFPKTSSWPNHDSNKGVTAACPHAGAKSFYKNLIW
LVKKGNSYPKLSKSYVNNKGKEVLVLWAIHHPSTSADQQSLYQNADAYVF
VGSSRYSRKFEPEIAARPKVRGQAGRMNYYWTLIEPGDTITFEATGNLVV
PRYAFAMNRGSGSGIIISDAPVHDCNTKCQTPKGAINTSLPFQNIHPVTI
GECPKYVKSTKLRMATGLRNIPSIQSRGLF SEQ ID NO: 6  (HA:124_Chimeric_H1N1|segment4:HA)
DTLCIGYHANNSTDTVDTVLEKNVTVTHSVNLLEDRHNGKLCKLGGIAPL
HLGKCNIAGWLLGNPECESLSTASSWSYIVETPSSDNGTCYPGDFIDYEE
LREQLSSVSSFERFEIFPKTSSWPNHDSNKGVTAACPYAGANSFYRNLIW
LVKKGNSYPKINKSYINNKEKEVLVLWAIHRPSTSADQQSLYQNADAYVF
VGSSRYSRKFEPEIATRPKVRDQAGRMNYYWTLVEPGDKITFEATGNLVV
PRYAFAMNRGSGSGIIISDAPVHDCNTKCQTPKGAINTSLPFQNIHPVTI
GECPKYVKSTKLRMATGLRNIPSIQSRGLF SEQ ID NO: 7  (HA:126_Chimeric_H1N1|segment4:HA)
DTLCIGYHANNSTDTVDTVLEKNVTVTHSVNLLEDKHNGKLCKLRGVAPL
HLGKCNIAGWLLGNPECESLSTASSWSYIVETSNSDNGTCYPGDFIDYEE
LREQLSSVSSFERFEIFPKTSSWPDHETNRGVTAACPYAGANSFYRNLIW
LVKKGNSYPKLSKSYINDKGKEVLVLWGIHHPSTSADQQSLYQNADAYVF
VGSSRYSRKFEPEIATRPKVRGQAGRMNYYWTLIEPGDTITFEATGNLVV
PRYAFAMNRGSGSGIIISDAPVHDCNTKCQTPKGAINTSLPFQNIHPVTI
GECPKYVKSTKLRMATGLRNIPSIQSRGLF SEQ ID NO: 8  (HA:129_Chimeric_H1N1|segment4:HA)
DTLCIGYHANNSTDTVDTVLEKNVTVTHSVNLLEDKHNGKLCKLRGVAPL
HLGKCNIAGWLLGNPECELLLTVSSWSYIVETSNSDNGTCYPGDFINYEE
LREQLSSVSSFERFEIFPKTSSWPDHETNRGVTAACPYAGANSFYRNLIW
LVKKGNSYPKLSKSYVNNKGKEVLVLWGIHHPPTSTDQQSLYQNADAYVF
VGSSRYSKKFKPEIAIRPKVRDQEGRMNYYWTLVEPGDKITFEATGNLVV
PRYAFAMERNAGSGIIISDTPVHDCNTTCQTPKGAINTSLPFQNIHPITI
GKCPKYVKSTKLRLATGLRNIPSIQSRGLF
```

SEQUENCE LISTING

SEQ ID NO: 9 (HA:208_Chimeric_H1N1|segment4:HA)
DTLCIGYHANNSTDTVDTVLEKNVTVTHSVNLLEDRHNGKLCKLGGIAPL
HLGKCNIAGWLLGNPECELLLTVSSWSYIVETSNSDNGTCYPGDFIDYEE
LREQLSSVSSFERFEIFPKTSSWPNHDTNRGVTAACPHAGTNSFYRNLIW
LVKKGNSYPKINKSYINNKEKEVLVLWAIHHPSTSADQQSLYQNADAYVF VGSSRYSKKFKPEIAIRPKVRDQEGRMNYYWTLVEPGDKITFEATGNLVV
PRYAFAMNRGSGSGIIISDAPVHDCNTKCQTPKGAINTSLPFQNIHPVTI
GECPKYVKSTKLRMATGLRNIPSIQSRGLF

SEQUENCE LISTING

<160> NUMBER OF SEQ ID NOS: 15

<210> SEQ ID NO 1
<211> LENGTH: 330
<212> TYPE: PRT
<213> ORGANISM: Artificial Sequence
<220> FEATURE:
<223> OTHER INFORMATION: Synthetic

<400> SEQUENCE: 1

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Arg His Asn Gly Lys Leu Cys Lys Leu Gly Gly Ile Ala
        35                  40                  45

Pro Leu His Leu Gly Lys Cys Asn Ile Ala Gly Trp Leu Leu Gly Asn
    50                  55                  60

Pro Glu Cys Glu Leu Leu Leu Thr Val Ser Ser Trp Ser Tyr Ile Val
65                  70                  75                  80

Glu Thr Ser Asn Ser Asp Asn Gly Thr Cys Tyr Pro Gly Asp Phe Ile
                85                  90                  95

Asn Tyr Glu Glu Leu Arg Glu Gln Leu Ser Ser Val Ser Ser Phe Glu
            100                 105                 110

Arg Phe Glu Ile Phe Pro Lys Thr Ser Ser Trp Pro Asp His Glu Thr
        115                 120                 125

Asn Arg Gly Val Thr Ala Ala Cys Pro His Ala Gly Ala Lys Ser Phe
    130                 135                 140

Tyr Arg Asn Leu Ile Trp Leu Val Lys Lys Gly Asn Ser Tyr Pro Lys
145                 150                 155                 160

Leu Ser Lys Ser Tyr Val Asn Asn Lys Gly Lys Glu Val Leu Val Leu
                165                 170                 175

Trp Gly Ile His His Pro Pro Thr Ser Thr Asp Gln Gln Ser Leu Tyr
            180                 185                 190

Gln Asn Ala Asp Ala Tyr Val Phe Val Gly Ser Ser Lys Tyr Asn Arg
        195                 200                 205

Lys Phe Lys Pro Glu Ile Ala Ala Arg Pro Lys Val Arg Asp Gln Glu
    210                 215                 220

Gly Arg Met Asn Tyr Tyr Trp Thr Leu Val Glu Pro Gly Asp Lys Ile
225                 230                 235                 240

Thr Phe Glu Ala Thr Gly Asn Leu Val Val Pro Arg Tyr Ala Phe Ala
                245                 250                 255

Met Asn Arg Gly Ser Gly Ser Gly Ile Ile Ile Ser Asp Ala Pro Val
            260                 265                 270

His Asp Cys Asn Thr Lys Cys Gln Thr Pro Lys Gly Ala Ile Asn Thr
        275                 280                 285

Ser Leu Pro Phe Gln Asn Ile His Pro Val Thr Ile Gly Glu Cys Pro

```
            290                 295                 300
Lys Tyr Val Lys Ser Thr Lys Leu Arg Met Ala Thr Gly Leu Arg Asn
305                 310                 315                 320

Ile Pro Ser Ile Gln Ser Arg Gly Leu Phe
                325                 330

<210> SEQ ID NO 2
<211> LENGTH: 330
<212> TYPE: PRT
<213> ORGANISM: Artificial Sequence
<220> FEATURE:
<223> OTHER INFORMATION: Synthetic

<400> SEQUENCE: 2

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
                20                  25                  30

Leu Glu Asp Lys His Asn Gly Lys Leu Cys Lys Leu Gly Gly Ile Ala
            35                  40                  45

Pro Leu His Leu Gly Lys Cys Asn Ile Ala Gly Trp Leu Leu Gly Asn
50                  55                  60

Pro Glu Cys Glu Leu Leu Leu Thr Val Ser Ser Trp Ser Tyr Ile Val
65                  70                  75                  80

Glu Thr Ser Asn Ser Asp Asn Gly Thr Cys Tyr Pro Gly Asp Phe Ile
                85                  90                  95

Asn Tyr Glu Glu Leu Arg Glu Gln Leu Ser Ser Val Ser Ser Phe Glu
            100                 105                 110

Arg Phe Glu Ile Phe Pro Lys Thr Ser Ser Trp Pro Asp His Glu Thr
        115                 120                 125

Asn Arg Gly Val Thr Ala Ala Cys Pro Tyr Ala Gly Ala Asn Ser Phe
    130                 135                 140

Tyr Arg Asn Leu Ile Trp Leu Val Lys Lys Gly Asn Ser Tyr Pro Lys
145                 150                 155                 160

Leu Ser Lys Ser Tyr Ile Asn Asp Lys Glu Lys Glu Val Leu Val Leu
                165                 170                 175

Trp Ala Ile His His Pro Ser Thr Ser Ala Asp Gln Gln Ser Leu Tyr
            180                 185                 190

Gln Asn Ala Asp Ala Tyr Val Phe Val Gly Ser Ser Arg Tyr Ser Lys
        195                 200                 205

Lys Phe Lys Pro Glu Ile Ala Ile Arg Pro Lys Val Arg Asp Gln Ala
    210                 215                 220

Gly Arg Met Asn Tyr Tyr Trp Thr Leu Val Glu Pro Gly Asp Lys Ile
225                 230                 235                 240

Thr Phe Glu Ala Thr Gly Asn Leu Val Val Pro Arg Tyr Ala Phe Ala
                245                 250                 255

Met Glu Arg Asn Ala Gly Ser Gly Ile Ile Ile Ser Asp Thr Ser Val
            260                 265                 270

His Asp Cys Asp Thr Thr Cys Gln Thr Pro Asn Gly Ala Ile Asn Thr
        275                 280                 285

Ser Leu Pro Phe Gln Asn Ile His Pro Val Thr Ile Gly Glu Cys Pro
    290                 295                 300

Lys Tyr Val Lys Ser Thr Lys Leu Arg Met Ala Thr Gly Leu Arg Asn
305                 310                 315                 320

Ile Pro Ser Ile Gln Ser Arg Gly Leu Phe
```

-continued

```
                325                 330

<210> SEQ ID NO 3
<211> LENGTH: 330
<212> TYPE: PRT
<213> ORGANISM: Artificial Sequence
<220> FEATURE:
<223> OTHER INFORMATION: Synthetic

<400> SEQUENCE: 3

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Lys His Asn Gly Lys Leu Cys Lys Leu Arg Gly Val Ala
        35                  40                  45

Pro Leu His Leu Gly Lys Cys Asn Ile Ala Gly Trp Leu Leu Gly Asn
    50                  55                  60

Pro Glu Cys Glu Leu Leu Leu Thr Val Ser Ser Trp Ser Tyr Ile Val
65                  70                  75                  80

Glu Thr Ser Asn Ser Asp Asn Gly Thr Cys Tyr Pro Gly Asp Phe Ile
                85                  90                  95

Asn Tyr Glu Glu Leu Arg Glu Gln Leu Ser Ser Val Ser Ser Phe Glu
            100                 105                 110

Arg Phe Glu Ile Phe Pro Lys Thr Ser Ser Trp Pro Asp His Glu Thr
        115                 120                 125

Asn Arg Gly Val Thr Ala Ala Cys Pro Tyr Ala Gly Ala Asn Ser Phe
    130                 135                 140

Tyr Arg Asn Leu Ile Trp Leu Val Lys Lys Gly Asn Ser Tyr Pro Lys
145                 150                 155                 160

Leu Ser Lys Ser Tyr Val Asn Asn Lys Gly Lys Glu Val Leu Val Leu
                165                 170                 175

Trp Gly Ile His His Pro Ser Thr Ser Ala Asp Gln Gln Ser Leu Tyr
            180                 185                 190

Gln Asn Ala Asp Ala Tyr Val Phe Val Gly Ser Ser Arg Tyr Ser Lys
        195                 200                 205

Lys Phe Lys Pro Glu Ile Ala Ile Arg Pro Lys Val Arg Asp Gln Glu
    210                 215                 220

Gly Arg Met Asn Tyr Tyr Trp Thr Leu Val Glu Pro Gly Asp Lys Ile
225                 230                 235                 240

Thr Phe Glu Ala Thr Gly Asn Leu Val Val Pro Arg Tyr Ala Phe Ala
                245                 250                 255

Met Glu Arg Asn Ala Gly Ser Gly Ile Ile Ile Ser Asp Thr Pro Val
            260                 265                 270

His Asp Cys Asn Thr Thr Cys Gln Thr Pro Lys Gly Ala Ile Asn Thr
        275                 280                 285

Ser Leu Pro Phe Gln Asn Ile His Pro Val Thr Ile Gly Glu Cys Pro
    290                 295                 300

Lys Tyr Val Lys Ser Thr Lys Leu Arg Met Ala Thr Gly Leu Arg Asn
305                 310                 315                 320

Ile Pro Ser Ile Gln Ser Arg Gly Leu Phe
                325                 330

<210> SEQ ID NO 4
<211> LENGTH: 330
<212> TYPE: PRT
```

<213> ORGANISM: Artificial Sequence
<220> FEATURE:
<223> OTHER INFORMATION: Synthetic

<400> SEQUENCE: 4

```
Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Arg His Asn Gly Lys Leu Cys Lys Leu Gly Gly Ile Ala
        35                  40                  45

Pro Leu His Leu Gly Lys Cys Asn Ile Ala Gly Trp Leu Leu Gly Asn
50                  55                  60

Pro Glu Cys Glu Leu Leu Leu Thr Val Ser Ser Trp Ser Tyr Ile Val
65                  70                  75                  80

Glu Thr Ser Asn Ser Asp Asn Gly Thr Cys Tyr Pro Gly Asp Phe Ile
                85                  90                  95

Asp Tyr Glu Glu Leu Arg Glu Gln Leu Ser Ser Val Ser Ser Phe Glu
            100                 105                 110

Arg Phe Glu Ile Phe Pro Lys Thr Ser Ser Trp Pro Asn His Asp Thr
        115                 120                 125

Asn Arg Gly Val Thr Ala Ala Cys Pro His Ala Gly Thr Asn Ser Phe
130                 135                 140

Tyr Arg Asn Leu Ile Trp Leu Val Lys Lys Gly Asn Ser Tyr Pro Lys
145                 150                 155                 160

Ile Asn Lys Ser Tyr Ile Asn Asn Lys Glu Lys Glu Val Leu Val Leu
                165                 170                 175

Trp Ala Ile His His Pro Ser Thr Ser Ala Asp Gln Gln Ser Leu Tyr
            180                 185                 190

Gln Asn Ala Asp Ala Tyr Val Phe Val Gly Ser Ser Arg Tyr Ser Lys
        195                 200                 205

Lys Phe Lys Pro Glu Ile Ala Ile Arg Pro Lys Val Arg Asp Gln Glu
210                 215                 220

Gly Arg Met Asn Tyr Tyr Trp Thr Leu Val Glu Pro Gly Asp Lys Ile
225                 230                 235                 240

Thr Phe Glu Ala Thr Gly Asn Leu Val Val Pro Arg Tyr Ala Phe Ala
                245                 250                 255

Met Asn Arg Gly Ser Gly Ser Gly Ile Ile Ile Ser Asp Ala Pro Val
            260                 265                 270

His Asp Cys Asn Thr Lys Cys Gln Thr Pro Lys Gly Ala Ile Asn Thr
        275                 280                 285

Ser Leu Pro Phe Gln Asn Ile His Pro Val Thr Ile Gly Glu Cys Pro
290                 295                 300

Lys Tyr Val Lys Ser Thr Lys Leu Arg Met Ala Thr Gly Leu Arg Asn
305                 310                 315                 320

Ile Pro Ser Ile Gln Ser Arg Gly Leu Phe
                325                 330
```

<210> SEQ ID NO 5
<211> LENGTH: 330
<212> TYPE: PRT
<213> ORGANISM: Artificial Sequence
<220> FEATURE:
<223> OTHER INFORMATION: Synthetic

<400> SEQUENCE: 5

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Lys His Asn Gly Lys Leu Cys Lys Leu Arg Gly Val Ala
            35                  40                  45

Pro Leu His Leu Gly Lys Cys Asn Ile Ala Gly Trp Ile Leu Gly Asn
50                  55                  60

Pro Glu Cys Glu Ser Leu Ser Thr Ala Ser Ser Trp Ser Tyr Ile Val
65                  70                  75                  80

Glu Thr Pro Ser Ser Asp Asn Gly Thr Cys Tyr Pro Gly Asp Phe Ile
                85                  90                  95

Asp Tyr Glu Glu Leu Arg Glu Gln Leu Ser Ser Val Ser Ser Phe Glu
            100                 105                 110

Arg Phe Glu Ile Phe Pro Lys Thr Ser Ser Trp Pro Asn His Asp Ser
            115                 120                 125

Asn Lys Gly Val Thr Ala Ala Cys Pro His Ala Gly Ala Lys Ser Phe
        130                 135                 140

Tyr Lys Asn Leu Ile Trp Leu Val Lys Lys Gly Asn Ser Tyr Pro Lys
145                 150                 155                 160

Leu Ser Lys Ser Tyr Val Asn Asn Lys Gly Lys Glu Val Leu Val Leu
                165                 170                 175

Trp Ala Ile His His Pro Ser Thr Ser Ala Asp Gln Gln Ser Leu Tyr
            180                 185                 190

Gln Asn Ala Asp Ala Tyr Val Phe Val Gly Ser Ser Arg Tyr Ser Arg
        195                 200                 205

Lys Phe Glu Pro Glu Ile Ala Ala Arg Pro Lys Val Arg Gly Gln Ala
210                 215                 220

Gly Arg Met Asn Tyr Tyr Trp Thr Leu Ile Glu Pro Gly Asp Thr Ile
225                 230                 235                 240

Thr Phe Glu Ala Thr Gly Asn Leu Val Val Pro Arg Tyr Ala Phe Ala
                245                 250                 255

Met Asn Arg Gly Ser Gly Ser Gly Ile Ile Ile Ser Asp Ala Pro Val
            260                 265                 270

His Asp Cys Asn Thr Lys Cys Gln Thr Pro Lys Gly Ala Ile Asn Thr
        275                 280                 285

Ser Leu Pro Phe Gln Asn Ile His Pro Val Thr Ile Gly Glu Cys Pro
290                 295                 300

Lys Tyr Val Lys Ser Thr Lys Leu Arg Met Ala Thr Gly Leu Arg Asn
305                 310                 315                 320

Ile Pro Ser Ile Gln Ser Arg Gly Leu Phe
                325                 330

<210> SEQ ID NO 6
<211> LENGTH: 330
<212> TYPE: PRT
<213> ORGANISM: Artificial Sequence
<220> FEATURE:
<223> OTHER INFORMATION: Synthetic

<400> SEQUENCE: 6

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

```
Leu Glu Asp Arg His Asn Gly Lys Leu Cys Lys Leu Gly Ile Ala
             35                  40                  45

Pro Leu His Leu Gly Lys Cys Asn Ile Ala Gly Trp Leu Leu Gly Asn
 50                  55                  60

Pro Glu Cys Glu Ser Leu Ser Thr Ala Ser Ser Trp Ser Tyr Ile Val
 65                  70                  75                  80

Glu Thr Pro Ser Ser Asp Asn Gly Thr Cys Tyr Pro Gly Asp Phe Ile
                 85                  90                  95

Asp Tyr Glu Glu Leu Arg Glu Gln Leu Ser Ser Val Ser Ser Phe Glu
            100                 105                 110

Arg Phe Glu Ile Phe Pro Lys Thr Ser Ser Trp Pro Asn His Asp Ser
            115                 120                 125

Asn Lys Gly Val Thr Ala Ala Cys Pro Tyr Ala Gly Ala Asn Ser Phe
        130                 135                 140

Tyr Arg Asn Leu Ile Trp Leu Val Lys Lys Gly Asn Ser Tyr Pro Lys
145                 150                 155                 160

Ile Asn Lys Ser Tyr Ile Asn Asn Lys Glu Lys Glu Val Leu Val Leu
                165                 170                 175

Trp Ala Ile His Arg Pro Ser Thr Ser Ala Asp Gln Gln Ser Leu Tyr
            180                 185                 190

Gln Asn Ala Asp Ala Tyr Val Phe Val Gly Ser Ser Arg Tyr Ser Arg
        195                 200                 205

Lys Phe Glu Pro Glu Ile Ala Thr Arg Pro Lys Val Arg Asp Gln Ala
    210                 215                 220

Gly Arg Met Asn Tyr Tyr Trp Thr Leu Val Glu Pro Gly Asp Lys Ile
225                 230                 235                 240

Thr Phe Glu Ala Thr Gly Asn Leu Val Val Pro Arg Tyr Ala Phe Ala
                245                 250                 255

Met Asn Arg Gly Ser Gly Ser Gly Ile Ile Ser Asp Ala Pro Val
            260                 265                 270

His Asp Cys Asn Thr Lys Cys Gln Thr Pro Lys Gly Ala Ile Asn Thr
        275                 280                 285

Ser Leu Pro Phe Gln Asn Ile His Pro Val Thr Ile Gly Glu Cys Pro
    290                 295                 300

Lys Tyr Val Lys Ser Thr Lys Leu Arg Met Ala Thr Gly Leu Arg Asn
305                 310                 315                 320

Ile Pro Ser Ile Gln Ser Arg Gly Leu Phe
                325                 330

<210> SEQ ID NO 7
<211> LENGTH: 330
<212> TYPE: PRT
<213> ORGANISM: Artificial Sequence
<220> FEATURE:
<223> OTHER INFORMATION: Synthetic

<400> SEQUENCE: 7

Asp Thr Leu Cys Ile Gly Tyr His Ala Asn Asn Ser Thr Asp Thr Val
 1               5                  10                  15

Asp Thr Val Leu Glu Lys Asn Val Thr Val Thr His Ser Val Asn Leu
                20                  25                  30

Leu Glu Asp Lys His Asn Gly Lys Leu Cys Lys Leu Arg Gly Val Ala
            35                  40                  45

Pro Leu His Leu Gly Lys Cys Asn Ile Ala Gly Trp Leu Leu Gly Asn
 50                  55                  60
```

```
Pro Glu Cys Glu Ser Leu Ser Thr Ala Ser Ser Trp Ser Tyr Ile Val
 65                  70                  75                  80

Glu Thr Ser Asn Ser Asp Asn Gly Thr Cys Tyr Pro Gly Asp Phe Ile
                 85                  90                  95

Asp Tyr Glu Glu Leu Arg Glu Gln Leu Ser Ser Val Ser Ser Phe Glu
            100                 105                 110

Arg Phe Glu Ile Phe Pro Lys Thr Ser Ser Trp Pro Asp His Glu Thr
        115                 120                 125

Asn Arg Gly Val Thr Ala Ala Cys Pro Tyr Ala Gly Ala Asn Ser Phe
    130                 135                 140

Tyr Arg Asn Leu Ile Trp Leu Val Lys Lys Gly Asn Ser Tyr Pro Lys
145                 150                 155                 160

Leu Ser Lys Ser Tyr Ile Asn Asp Lys Gly Lys Glu Val Leu Val Leu
                165                 170                 175

Trp Gly Ile His His Pro Ser Thr Ser Ala Asp Gln Gln Ser Leu Tyr
            180                 185                 190

Gln Asn Ala Asp Ala Tyr Val Phe Val Gly Ser Ser Arg Tyr Ser Arg
        195                 200                 205

Lys Phe Glu Pro Glu Ile Ala Thr Arg Pro Lys Val Arg Gly Gln Ala
    210                 215                 220

Gly Arg Met Asn Tyr Tyr Trp Thr Leu Ile Glu Pro Gly Asp Thr Ile
225                 230                 235                 240

Thr Phe Glu Ala Thr Gly Asn Leu Val Val Pro Arg Tyr Ala Phe Ala
                245                 250                 255

Met Asn Arg Gly Ser Gly Ser Gly Ile Ile Ile Ser Asp Ala Pro Val
            260                 265                 270

His Asp Cys Asn Thr Lys Cys Gln Thr Pro Lys Gly Ala Ile Asn Thr
        275                 280                 285

Ser Leu Pro Phe Gln Asn Ile His Pro Val Thr Ile Gly Glu Cys Pro
    290                 295                 300

Lys Tyr Val Lys Ser Thr Lys Leu Arg Met Ala Thr Gly Leu Arg Asn
305                 310                 315                 320

Ile Pro Ser Ile Gln Ser Arg Gly Leu Phe
                325                 330

<210> SEQ ID NO 8
<211> LENGTH: 330
<212> TYPE: PRT
<213> ORGANISM: Artificial Sequence
<220> FEATURE:
<223> OTHER INFORMATION: Synthetic

<400> SEQUENCE: 8

Asp Thr Leu Cys Ile Gly Tyr His Ala Asn Asn Ser Thr Asp Thr Val
 1               5                  10                  15

Asp Thr Val Leu Glu Lys Asn Val Thr Val Thr His Ser Val Asn Leu
                 20                  25                  30

Leu Glu Asp Lys His Asn Gly Lys Leu Cys Lys Leu Arg Gly Val Ala
             35                  40                  45

Pro Leu His Leu Gly Lys Cys Asn Ile Ala Gly Trp Leu Leu Gly Asn
         50                  55                  60

Pro Glu Cys Glu Leu Leu Leu Thr Val Ser Ser Trp Ser Tyr Ile Val
 65                  70                  75                  80

Glu Thr Ser Asn Ser Asp Asn Gly Thr Cys Tyr Pro Gly Asp Phe Ile
                 85                  90                  95
```

```
Asn Tyr Glu Glu Leu Arg Glu Gln Leu Ser Ser Val Ser Ser Phe Glu
            100                 105                 110

Arg Phe Glu Ile Phe Pro Lys Thr Ser Ser Trp Pro Asp His Glu Thr
        115                 120                 125

Asn Arg Gly Val Thr Ala Ala Cys Pro Tyr Ala Gly Ala Asn Ser Phe
    130                 135                 140

Tyr Arg Asn Leu Ile Trp Leu Val Lys Lys Gly Asn Ser Tyr Pro Lys
145                 150                 155                 160

Leu Ser Lys Ser Tyr Val Asn Asn Lys Gly Lys Glu Val Leu Val Leu
                165                 170                 175

Trp Gly Ile His His Pro Pro Thr Ser Thr Asp Gln Gln Ser Leu Tyr
            180                 185                 190

Gln Asn Ala Asp Ala Tyr Val Phe Val Gly Ser Ser Arg Tyr Ser Lys
        195                 200                 205

Lys Phe Lys Pro Glu Ile Ala Ile Arg Pro Lys Val Arg Asp Gln Glu
    210                 215                 220

Gly Arg Met Asn Tyr Tyr Trp Thr Leu Val Glu Pro Gly Asp Lys Ile
225                 230                 235                 240

Thr Phe Glu Ala Thr Gly Asn Leu Val Val Pro Arg Tyr Ala Phe Ala
                245                 250                 255

Met Glu Arg Asn Ala Gly Ser Gly Ile Ile Ile Ser Asp Thr Pro Val
            260                 265                 270

His Asp Cys Asn Thr Thr Cys Gln Thr Pro Lys Gly Ala Ile Asn Thr
        275                 280                 285

Ser Leu Pro Phe Gln Asn Ile His Pro Ile Thr Ile Gly Lys Cys Pro
    290                 295                 300

Lys Tyr Val Lys Ser Thr Lys Leu Arg Leu Ala Thr Gly Leu Arg Asn
305                 310                 315                 320

Ile Pro Ser Ile Gln Ser Arg Gly Leu Phe
                325                 330

<210> SEQ ID NO 9
<211> LENGTH: 330
<212> TYPE: PRT
<213> ORGANISM: Artificial Sequence
<220> FEATURE:
<223> OTHER INFORMATION: Synthetic

<400> SEQUENCE: 9

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
                20                  25                  30

Leu Glu Asp Arg His Asn Gly Lys Leu Cys Lys Leu Gly Gly Ile Ala
            35                  40                  45

Pro Leu His Leu Gly Lys Cys Asn Ile Ala Gly Trp Leu Leu Gly Asn
        50                  55                  60

Pro Glu Cys Glu Leu Leu Leu Thr Val Ser Ser Trp Ser Tyr Ile Val
65                  70                  75                  80

Glu Thr Ser Asn Ser Asp Asn Gly Thr Cys Tyr Pro Gly Asp Phe Ile
                85                  90                  95

Asp Tyr Glu Glu Leu Arg Glu Gln Leu Ser Ser Val Ser Ser Phe Glu
            100                 105                 110

Arg Phe Glu Ile Phe Pro Lys Thr Ser Ser Trp Pro Asn His Asp Thr
        115                 120                 125
```

```
Asn Arg Gly Val Thr Ala Ala Cys Pro His Ala Gly Thr Asn Ser Phe
130                 135                 140
Tyr Arg Asn Leu Ile Trp Leu Val Lys Gly Asn Ser Tyr Pro Lys
145                 150                 155                 160
Ile Asn Lys Ser Tyr Ile Asn Asn Lys Glu Lys Glu Val Leu Val Leu
                165                 170                 175
Trp Ala Ile His His Pro Ser Thr Ser Ala Asp Gln Gln Ser Leu Tyr
            180                 185                 190
Gln Asn Ala Asp Ala Tyr Val Phe Val Gly Ser Ser Arg Tyr Ser Lys
        195                 200                 205
Lys Phe Lys Pro Glu Ile Ala Ile Arg Pro Lys Val Arg Asp Gln Glu
210                 215                 220
Gly Arg Met Asn Tyr Tyr Trp Thr Leu Val Glu Pro Gly Asp Lys Ile
225                 230                 235                 240
Thr Phe Glu Ala Thr Gly Asn Leu Val Val Pro Arg Tyr Ala Phe Ala
                245                 250                 255
Met Asn Arg Gly Ser Gly Ser Gly Ile Ile Ile Ser Asp Ala Pro Val
            260                 265                 270
His Asp Cys Asn Thr Lys Cys Gln Thr Pro Lys Gly Ala Ile Asn Thr
        275                 280                 285
Ser Leu Pro Phe Gln Asn Ile His Pro Val Thr Ile Gly Glu Cys Pro
290                 295                 300
Lys Tyr Val Lys Ser Thr Lys Leu Arg Met Ala Thr Gly Leu Arg Asn
305                 310                 315                 320
Ile Pro Ser Ile Gln Ser Arg Gly Leu Phe
                325                 330

<210> SEQ ID NO 10
<211> LENGTH: 549
<212> TYPE: PRT
<213> ORGANISM: Influenza A virus

<400> SEQUENCE: 10

Asp Thr Leu Cys Ile Gly Tyr His Ala Asn Asn Ser Thr Asp Thr Val
1               5                   10                  15
Asp Thr Val Leu Glu Lys Asn Val Thr Val Thr His Ser Val Asn Leu
                20                  25                  30
Leu Glu Asp Lys His Asn Gly Lys Leu Cys Lys Leu Arg Gly Val Ala
            35                  40                  45
Pro Leu His Leu Gly Lys Cys Asn Ile Ala Gly Trp Ile Leu Gly Asn
50                  55                  60
Pro Glu Cys Glu Ser Leu Ser Thr Ala Ser Ser Trp Ser Tyr Ile Val
65                  70                  75                  80
Glu Thr Ser Ser Ser Asp Asn Gly Thr Cys Tyr Pro Gly Asp Phe Ile
                85                  90                  95
Asp Tyr Glu Glu Leu Arg Glu Gln Leu Ser Ser Val Ser Ser Phe Glu
            100                 105                 110
Arg Phe Glu Ile Phe Pro Lys Thr Ser Ser Trp Pro Asn His Asp Ser
        115                 120                 125
Asn Lys Gly Val Thr Ala Ala Cys Pro His Ala Gly Ala Lys Ser Phe
130                 135                 140
Tyr Lys Asn Leu Ile Trp Leu Val Lys Lys Gly Asn Ser Tyr Pro Lys
145                 150                 155                 160
Leu Ser Lys Ser Tyr Ile Asn Asp Lys Gly Lys Glu Val Leu Val Leu
                165                 170                 175
```

Trp Gly Ile His His Pro Ser Thr Ser Ala Asp Gln Gln Ser Leu Tyr
            180                 185                 190

Gln Asn Ala Asp Ala Tyr Val Phe Val Gly Thr Ser Arg Tyr Ser Lys
        195                 200                 205

Lys Phe Lys Pro Glu Ile Ala Ile Arg Pro Lys Val Arg Asp Gln Glu
210                 215                 220

Gly Arg Met Asn Tyr Tyr Trp Thr Leu Val Glu Pro Gly Asp Lys Ile
225                 230                 235                 240

Thr Phe Glu Ala Thr Gly Asn Leu Val Val Pro Arg Tyr Ala Phe Ala
                245                 250                 255

Met Glu Arg Asn Ala Gly Ser Gly Ile Ile Ile Ser Asp Thr Pro Val
            260                 265                 270

His Asn Cys Asn Thr Thr Cys Gln Thr Pro Lys Gly Ala Ile Asn Thr
        275                 280                 285

Ser Leu Pro Phe Gln Asn Ile His Pro Ile Thr Ile Gly Lys Cys Pro
    290                 295                 300

Lys Tyr Val Lys Ser Thr Lys Leu Arg Leu Ala Thr Gly Leu Arg Asn
305                 310                 315                 320

Val Pro Ser Ile Gln Ser Arg Gly Leu Phe Gly Ala Ile Ala Gly Phe
                325                 330                 335

Ile Glu Gly Gly Trp Thr Gly Met Val Asp Gly Trp Tyr Gly Tyr His
            340                 345                 350

His Gln Asn Glu Gln Gly Ser Gly Tyr Ala Ala Asp Leu Lys Ser Thr
        355                 360                 365

Gln Asn Ala Ile Asp Glu Ile Thr Asn Lys Val Asn Ser Val Ile Glu
    370                 375                 380

Lys Met Asn Thr Gln Phe Thr Ala Val Gly Lys Glu Phe Asn His Leu
385                 390                 395                 400

Glu Lys Arg Ile Glu Asn Leu Asn Lys Lys Val Asp Asp Gly Phe Leu
                405                 410                 415

Asp Ile Trp Thr Tyr Asn Ala Glu Leu Leu Val Leu Leu Glu Asn Glu
            420                 425                 430

Arg Thr Leu Asp Tyr His Asp Ser Asn Val Lys Asn Leu Tyr Glu Lys
        435                 440                 445

Val Arg Ser Gln Leu Lys Asn Asn Ala Lys Glu Ile Gly Asn Gly Cys
    450                 455                 460

Phe Glu Phe Tyr His Lys Cys Asp Asn Thr Cys Met Glu Ser Val Lys
465                 470                 475                 480

Asn Gly Thr Tyr Asp Tyr Pro Lys Tyr Ser Glu Glu Ala Lys Leu Asn
                485                 490                 495

Arg Glu Glu Ile Asp Gly Val Lys Leu Glu Ser Thr Arg Ile Tyr Gln
            500                 505                 510

Ile Leu Ala Ile Tyr Ser Thr Val Ala Ser Ser Leu Val Leu Val Val
        515                 520                 525

Ser Leu Gly Ala Ile Ser Phe Trp Met Cys Ser Asn Gly Ser Leu Gln
    530                 535                 540

Cys Arg Ile Cys Ile
545

<210> SEQ ID NO 11
<211> LENGTH: 549
<212> TYPE: PRT
<213> ORGANISM: Influenza A virus

```
<400> SEQUENCE: 11

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Arg His Asn Gly Lys Leu Cys Lys Leu Arg Gly Val Ala
        35                  40                  45

Pro Leu His Leu Gly Lys Cys Asn Ile Ala Gly Trp Leu Leu Gly Asn
    50                  55                  60

Pro Glu Cys Glu Ser Leu Ser Thr Ala Ser Ser Trp Ser Tyr Ile Val
65                  70                  75                  80

Glu Thr Ser Asn Ser Asp Asn Gly Thr Cys Tyr Pro Gly Asp Phe Ile
                85                  90                  95

Asn Tyr Glu Glu Leu Arg Glu Gln Leu Ser Ser Val Ser Ser Phe Glu
            100                 105                 110

Arg Phe Glu Ile Phe Pro Lys Thr Ser Ser Trp Pro Asn His Asp Thr
        115                 120                 125

Asn Arg Gly Val Thr Ala Ala Cys Pro His Ala Gly Thr Asn Ser Phe
    130                 135                 140

Tyr Arg Asn Leu Ile Trp Leu Val Lys Lys Gly Asn Ser Tyr Pro Lys
145                 150                 155                 160

Ile Asn Lys Ser Tyr Ile Asn Asn Lys Glu Lys Glu Val Leu Val Leu
                165                 170                 175

Trp Ala Ile His His Pro Ser Thr Ser Ala Asp Gln Gln Ser Leu Tyr
            180                 185                 190

Gln Asn Ala Asp Ala Tyr Val Phe Val Gly Ser Ser Arg Tyr Ser Arg
        195                 200                 205

Lys Phe Glu Pro Glu Ile Ala Thr Arg Pro Lys Val Arg Asp Gln Ala
    210                 215                 220

Gly Arg Met Asn Tyr Tyr Trp Thr Leu Val Glu Pro Gly Asp Lys Ile
225                 230                 235                 240

Thr Phe Glu Ala Thr Gly Asn Leu Val Val Pro Arg Tyr Ala Phe Ala
                245                 250                 255

Leu Lys Arg Asn Ser Gly Ser Gly Ile Ile Ser Asp Thr Ser Val
            260                 265                 270

His Asp Cys Asp Thr Thr Cys Gln Thr Pro Asn Gly Ala Ile Asn Thr
        275                 280                 285

Ser Leu Pro Phe Gln Asn Ile His Pro Val Thr Ile Gly Glu Cys Pro
    290                 295                 300

Lys Tyr Val Lys Ser Thr Lys Leu Arg Met Ala Thr Gly Leu Arg Asn
305                 310                 315                 320

Ile Pro Ser Ile Gln Ser Arg Gly Leu Phe Gly Ala Ile Ala Gly Phe
                325                 330                 335

Ile Glu Gly Gly Trp Thr Gly Met Ile Asp Gly Trp Tyr Gly Tyr His
            340                 345                 350

His Gln Asn Glu Gln Gly Ser Gly Tyr Ala Ala Asp Leu Lys Ser Thr
        355                 360                 365

Gln Asn Ala Ile Asp Gly Ile Thr Asn Lys Val Asn Ser Val Ile Glu
    370                 375                 380

Lys Met Asn Thr Gln Phe Thr Ala Val Gly Lys Glu Phe Ser His Leu
385                 390                 395                 400

Glu Arg Arg Ile Glu Asn Leu Asn Lys Lys Val Asp Asp Gly Phe Leu
                405                 410                 415
```

-continued

```
Asp Ile Trp Thr Tyr Asn Ala Glu Leu Leu Val Leu Leu Glu Asn Glu
            420                 425                 430

Arg Thr Leu Asp Tyr His Asp Ser Asn Val Lys Asn Leu Tyr Glu Lys
        435                 440                 445

Val Arg Ser Gln Leu Lys Asn Asn Ala Lys Glu Ile Gly Asn Gly Cys
450                 455                 460

Phe Glu Phe Tyr His Lys Cys Asp Asp Thr Cys Met Glu Ser Val Lys
465                 470                 475                 480

Asn Gly Thr Tyr Asp Tyr Pro Lys Tyr Ser Glu Glu Ala Lys Leu Asn
                485                 490                 495

Arg Glu Glu Ile Asp Gly Val Lys Leu Glu Ser Thr Arg Ile Tyr Gln
            500                 505                 510

Ile Leu Ala Ile Tyr Ser Thr Val Ala Ser Ser Leu Val Leu Val Val
        515                 520                 525

Ser Leu Gly Ala Ile Ser Phe Trp Met Cys Ser Asn Gly Ser Leu Gln
530                 535                 540

Cys Arg Ile Cys Ile
545

<210> SEQ ID NO 12
<211> LENGTH: 549
<212> TYPE: PRT
<213> ORGANISM: Influenza A virus

<400> SEQUENCE: 12

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Arg His Asn Gly Lys Leu Cys Lys Leu Gly Gly Ile Ala
        35                  40                  45

Pro Leu His Leu Gly Lys Cys Asn Ile Ala Gly Trp Leu Leu Gly Asn
    50                  55                  60

Pro Glu Cys Glu Leu Leu Leu Thr Val Ser Ser Trp Ser Tyr Ile Val
65                  70                  75                  80

Glu Thr Ser Asn Ser Asp Asn Gly Thr Cys Tyr Pro Gly Asp Phe Ile
                85                  90                  95

Asn Tyr Glu Glu Leu Arg Glu Gln Leu Ser Ser Val Ser Ser Phe Glu
            100                 105                 110

Arg Phe Glu Ile Phe Pro Lys Thr Ser Ser Trp Pro Asn His Glu Thr
        115                 120                 125

Asn Arg Gly Val Thr Ala Ala Cys Pro Tyr Ala Gly Ala Asn Ser Phe
    130                 135                 140

Tyr Arg Asn Leu Ile Trp Leu Val Glu Lys Gly Asn Ser Tyr Pro Lys
145                 150                 155                 160

Leu Ser Lys Ser Tyr Val Asn Asn Lys Gly Lys Glu Val Leu Val Leu
                165                 170                 175

Trp Gly Ile His His Pro Pro Thr Ser Thr Asp Gln Gln Ser Leu Tyr
            180                 185                 190

Gln Asn Ala Asp Ala Tyr Val Phe Val Gly Ser Ser Lys Tyr Asn Arg
        195                 200                 205

Lys Phe Lys Pro Glu Ile Ala Ala Arg Pro Lys Val Arg Gly Gln Ala
    210                 215                 220

Gly Arg Met Asn Tyr Tyr Trp Thr Leu Ile Glu Pro Gly Asp Thr Ile
```

```
            225                 230                 235                 240
        Thr Phe Glu Ala Thr Gly Asn Leu Val Val Pro Arg Tyr Ala Phe Ala
                        245                 250                 255

Met Asn Arg Gly Ser Gly Ser Gly Ile Ile Ile Ser Asp Ala Pro Val
                        260                 265                 270

His Asp Cys Asn Thr Lys Cys Gln Thr Pro Lys Gly Ala Ile Asn Thr
                        275                 280                 285

Ser Leu Pro Phe Gln Asn Ile His Pro Val Thr Ile Gly Glu Cys Pro
                        290                 295                 300

Lys Tyr Val Lys Ser Thr Lys Leu Arg Met Ala Thr Gly Leu Arg Asn
        305                 310                 315                 320

Ile Pro Ser Ile Gln Ser Arg Gly Leu Phe Gly Ala Ile Ala Gly Phe
                        325                 330                 335

Ile Glu Gly Gly Trp Thr Gly Met Ile Asp Gly Trp Tyr Gly Tyr His
                        340                 345                 350

His Gln Asn Glu Gln Gly Ser Gly Tyr Ala Ala Asp Gln Arg Ser Thr
                        355                 360                 365

Gln Asn Ala Ile Asp Gly Ile Thr Asn Lys Val Asn Ser Val Ile Glu
                        370                 375                 380

Lys Met Asn Thr Gln Phe Thr Ala Val Gly Lys Glu Phe Asn His Leu
        385                 390                 395                 400

Glu Lys Arg Ile Glu Asn Leu Asn Lys Lys Val Asp Asp Gly Phe Leu
                        405                 410                 415

Asp Ile Trp Thr Tyr Asn Ala Glu Leu Leu Val Leu Leu Glu Asn Glu
                        420                 425                 430

Arg Thr Leu Asp Phe His Asp Ser Asn Val Lys Asn Leu Tyr Glu Lys
                        435                 440                 445

Val Arg Ser Gln Leu Arg Asn Asn Ala Lys Glu Ile Gly Asn Gly Cys
                        450                 455                 460

Phe Glu Phe Tyr His Lys Cys Asp Asp Thr Cys Met Glu Ser Val Lys
        465                 470                 475                 480

Asn Gly Thr Tyr Asp Tyr Pro Lys Tyr Ser Glu Glu Ser Lys Leu Asn
                        485                 490                 495

Arg Glu Glu Ile Asp Gly Val Lys Leu Glu Ser Thr Arg Ile Tyr Gln
                        500                 505                 510

Ile Leu Ala Ile Tyr Ser Thr Val Ala Ser Ser Leu Val Leu Leu Val
                        515                 520                 525

Ser Leu Gly Ala Ile Ser Phe Trp Met Cys Ser Asn Gly Ser Leu Gln
                        530                 535                 540

Cys Arg Ile Cys Ile
        545

<210> SEQ ID NO 13
<211> LENGTH: 549
<212> TYPE: PRT
<213> ORGANISM: Influenza A virus

<400> SEQUENCE: 13

Asp Thr Leu Cys Ile Gly Tyr His Ala Asn Asn Ser Thr Asp Thr Val
        1               5                   10                  15

Asp Thr Val Leu Glu Lys Asn Val Thr Val Thr His Ser Val Asn Leu
                        20                  25                  30

Leu Glu Asn Lys His Asp Gly Lys Leu Cys Lys Leu Arg Gly Val Ala
                        35                  40                  45
```

-continued

```
Pro Leu His Leu Gly Lys Cys Asn Ile Ala Gly Trp Leu Leu Gly Asn
    50                  55                  60
Pro Glu Cys Glu Ser Leu Phe Thr Ala Ser Ser Trp Ser Tyr Ile Val
 65              70                  75                  80
Glu Thr Pro Asn Ser Asp Asn Gly Thr Cys Tyr Pro Gly Asp Phe Ile
                 85                  90                  95
Asn Tyr Glu Glu Leu Arg Glu His Leu Ser Ser Val Ser Ser Phe Glu
             100                 105                 110
Arg Phe Glu Ile Phe Pro Lys Ala Asn Ser Trp Pro Asn His Asp Thr
         115                 120                 125
Asn Lys Gly Val Thr Ala Ala Cys Pro Tyr Ala Gly Ala Asn Ser Phe
    130                 135                 140
Tyr Arg Asn Leu Ile Trp Leu Val Lys Lys Gly Asn Ser Tyr Pro Lys
145                 150                 155                 160
Leu Ser Lys Ser Tyr Ile Asn Asn Lys Lys Glu Val Leu Val Ile
                165                 170                 175
Trp Gly Ile His His Pro Pro Thr Ser Thr Asp Gln Gln Thr Leu Tyr
            180                 185                 190
Gln Asn Ala Asp Ala Tyr Val Phe Val Gly Ser Ser Lys Tyr Ser Lys
        195                 200                 205
Arg Phe Lys Pro Glu Ile Ala Ala Arg Pro Lys Val Arg Asn Gln Ala
    210                 215                 220
Gly Arg Met Asn Tyr Tyr Trp Thr Leu Ile Glu Pro Gly Asp Thr Ile
225                 230                 235                 240
Thr Phe Glu Ala Thr Gly Asn Leu Val Val Pro Arg Tyr Ala Phe Ala
                245                 250                 255
Met Lys Arg Gly Ser Gly Ser Gly Ile Ile Val Ser Asp Ala Pro Val
            260                 265                 270
His Asp Cys Asn Thr Thr Cys Gln Thr Pro Lys Gly Ala Ile Asn Thr
        275                 280                 285
Ser Leu Pro Phe Gln Asn Ile His Pro Val Thr Ile Gly Glu Cys Pro
    290                 295                 300
Lys Tyr Val Lys Ser Thr Lys Leu Arg Met Ala Thr Gly Leu Arg Asn
305                 310                 315                 320
Ile Pro Ser Ile Gln Ser Arg Gly Leu Phe Gly Ala Ile Ala Gly Phe
                325                 330                 335
Leu Glu Gly Gly Trp Thr Gly Met Ile Asp Gly Trp Tyr Gly Tyr His
            340                 345                 350
His Gln Asn Glu Gln Gly Ser Gly Tyr Ala Ala Asp Gln Lys Ser Thr
        355                 360                 365
Gln Asn Ala Ile Asp Gly Ile Thr Asn Lys Val Asn Ser Ile Ile Glu
    370                 375                 380
Lys Met Asn Thr Gln Phe Thr Ala Val Gly Lys Glu Phe Asn Gln Leu
385                 390                 395                 400
Glu Lys Arg Ile Glu Ser Leu Asn Asn Lys Val Asp Asp Gly Phe Leu
                405                 410                 415
Asp Ile Trp Thr Tyr Asn Ala Glu Met Leu Val Leu Leu Glu Asn Glu
            420                 425                 430
Arg Thr Leu Asp Tyr His Asp Ser Asn Val Lys Asn Leu Tyr Glu Lys
        435                 440                 445
Val Arg Ser Gln Leu Lys Asn Asn Ala Lys Glu Ile Gly Asn Gly Cys
    450                 455                 460
Phe Glu Phe Tyr His Lys Cys Asp Asn Thr Cys Met Glu Ser Val Lys
```

```
                465                 470                 475                 480
Asn Gly Thr Tyr Asp Tyr Pro Lys Tyr Ser Glu Glu Ala Lys

UNITED STATES PATENT AND TRADEMARK OFFICE
CERTIFICATE OF CORRECTION

| | | |
|---|---|---|
| PATENT NO. | : 9,981,034 B2 | Page 1 of 1 |
| APPLICATION NO. | : 15/131989 | |
| DATED | : May 29, 2018 | |
| INVENTOR(S) | : Huber et al. | |

It is certified that error appears in the above-identified patent and that said Letters Patent is hereby corrected as shown below:

In the Specification

At Column 1 In the Government Support clause:
Line 17
DELETE      "Grant No. 1 R15 AI090582-01"
INSERT      --Grant No. R15 AI090582--
Lines 19-20
DELETE      "and Project #15-020 from the National Pork Board"
Lines 20-21
DELETE      "Accordingly, the government has certain rights in this invention."
INSERT      --The government has certain rights in the invention.--

Signed and Sealed this
Twenty-first Day of April, 2020

Andrei Iancu
*Director of the United States Patent and Trademark Office*